(12) United States Patent
Frankel

(10) Patent No.: US 9,603,634 B1
(45) Date of Patent: Mar. 28, 2017

(54) PERCUTANEOUS ROD-TO-ROD CROSS CONNECTOR

(71) Applicant: Amendia, Inc., Marietta, GA (US)

(72) Inventor: Bruce Frankel, Mount Pleasant, SC (US)

(73) Assignee: Amendia, Inc., Marietta, GA (US)

( * ) Notice: Subject to any disclaimer, the term of this patent is extended or adjusted under 35 U.S.C. 154(b) by 0 days.

(21) Appl. No.: 15/065,927

(22) Filed: Mar. 10, 2016

Related U.S. Application Data

(63) Continuation of application No. 14/941,135, filed on Nov. 13, 2015.

(51) Int. Cl.
*A61B 17/70* (2006.01)

(52) U.S. Cl.
CPC ...... *A61B 17/7043* (2013.01); *A61B 17/7032* (2013.01); *A61B 17/7083* (2013.01)

(58) Field of Classification Search
CPC ............ A61B 17/7007; A61B 17/7008; A61B 17/7041; A61B 17/7043; A61B 17/7049; A61B 17/705; A61B 17/7052; A61B 17/7001; A61B 17/7014; A61B 17/7032; A61B 17/7034; A61B 17/7035; A61B 17/7037; A61B 17/7038; A61B 17/704; A61B 17/7046; A61B 17/8685

See application file for complete search history.

(56) References Cited

U.S. PATENT DOCUMENTS

| | | |
|---|---|---|
| 5,885,286 A | 3/1999 | Sherman et al. |
| 6,224,598 B1 | 5/2001 | Jackson |
| 6,485,491 B1 | 11/2002 | Farris et al. |
| 6,676,661 B1 | 1/2004 | Martin Benlloch et al. |
| 7,163,538 B2 | 1/2007 | Altarac et al. |
| 7,204,838 B2 | 4/2007 | Jackson |
| 7,645,294 B2 | 1/2010 | Kalfas et al. |
| 7,691,145 B2 | 4/2010 | Reiley et al. |
| 7,717,939 B2 | 5/2010 | Ludwig et al. |
| 7,833,251 B1 | 11/2010 | Ahlgren et al. |
| 7,896,902 B2 | 3/2011 | Jeon et al. |
| RE42,545 E | 7/2011 | Ralph et al. |
| 8,012,184 B2 | 9/2011 | Schlapfer et al. |
| 8,100,909 B2 | 1/2012 | Butler et al. |
| 8,197,512 B1 | 6/2012 | Hunt et al. |
| 8,758,411 B1 | 6/2014 | Rayon et al. |

(Continued)

*Primary Examiner* — Lynnsy Summitt
*Assistant Examiner* — Lynnsy Schneider
(74) *Attorney, Agent, or Firm* — David L. King

(57) ABSTRACT

A percutaneous cross connector system for use with implantation rods comprising a rod attachment device comprising a first jaw portion and a second jaw portion. The first jaw portion comprises a first concave surface to engage with a surface of a rod, a first biasing member, and a first pivoting mechanism. The second jaw portion comprises a second concave surface to engage with an opposite surface of the rod from the first jaw portion, a second pivoting mechanism, a second biasing surface, and a second locking surface. The first and second jaw portions can be mated so that the first and second concave surfaces are positioned on opposite sides of the rod, the first and second pivoting mechanisms are aligned to pivot on a common axis, and the first biasing member is engaged against the second biasing surface to drive the second jaw portion against the rod.

22 Claims, 16 Drawing Sheets

(56) References Cited

U.S. PATENT DOCUMENTS

| | | |
|---|---|---|
| 8,852,241 B2 | 10/2014 | Datta |
| 2003/0004512 A1 | 1/2003 | Farris et al. |
| 2003/0199873 A1 | 10/2003 | Richelsoph |
| 2004/0116928 A1 | 6/2004 | Young et al. |
| 2005/0113831 A1* | 5/2005 | Franck ............... A61B 17/7052 606/250 |
| 2005/0240265 A1 | 10/2005 | Kuiper et al. |
| 2006/0064091 A1 | 3/2006 | Ludwig et al. |
| 2007/0073291 A1 | 3/2007 | Cordaro et al. |
| 2007/0233078 A1 | 10/2007 | Justis et al. |
| 2007/0250061 A1 | 10/2007 | Chin et al. |
| 2007/0270832 A1 | 11/2007 | Moore |
| 2007/0276374 A1 | 11/2007 | Broman et al. |
| 2008/0071274 A1 | 3/2008 | Ensign |
| 2008/0097441 A1 | 4/2008 | Hayes et al. |
| 2008/0119858 A1 | 5/2008 | Potash |
| 2008/0177318 A1 | 7/2008 | Veldman et al. |
| 2008/0221622 A1 | 9/2008 | Triplett et al. |
| 2008/0306513 A1 | 12/2008 | Winslow et al. |
| 2008/0306527 A1 | 12/2008 | Winslow et al. |
| 2008/0312692 A1 | 12/2008 | Brennan et al. |
| 2009/0024169 A1 | 1/2009 | Triplett et al. |
| 2009/0030463 A1 | 1/2009 | Samudrala et al. |
| 2009/0036934 A1 | 2/2009 | Biedermann et al. |
| 2009/0069852 A1 | 3/2009 | Farris et al. |
| 2009/0105760 A1 | 4/2009 | Frey |
| 2009/0118772 A1 | 5/2009 | Diederich et al. |
| 2009/0216277 A1 | 8/2009 | Tornier et al. |
| 2009/0254125 A1 | 10/2009 | Predick |
| 2009/0264926 A1 | 10/2009 | Taylor et al. |
| 2009/0299411 A1 | 12/2009 | Laskowitz et al. |
| 2010/0030270 A1 | 2/2010 | Winslow et al. |
| 2010/0036417 A1 | 2/2010 | James et al. |
| 2010/0036432 A1 | 2/2010 | Ely |
| 2010/0036436 A1 | 2/2010 | Winslow et al. |
| 2010/0042152 A1 | 2/2010 | Semler et al. |
| 2010/0057131 A1 | 3/2010 | Ely et al. |
| 2010/0057135 A1 | 3/2010 | Helges et al. |
| 2010/0057136 A1 | 3/2010 | Helges et al. |
| 2010/0094345 A1 | 4/2010 | Saidha et al. |
| 2010/0160981 A1 | 6/2010 | Butler et al. |
| 2010/0222822 A1 | 9/2010 | Farris et al. |
| 2010/0280552 A1 | 11/2010 | Lee |
| 2010/0298884 A1 | 11/2010 | Faizan et al. |
| 2011/0106178 A1 | 5/2011 | Schwab |
| 2011/0137345 A1 | 6/2011 | Stoll et al. |
| 2011/0178558 A1 | 7/2011 | Barry |
| 2011/0213419 A1 | 9/2011 | Richelsoph |
| 2011/0218579 A1 | 9/2011 | Jackson |
| 2012/0095510 A1 | 4/2012 | Nihalani |
| 2012/0095511 A1 | 4/2012 | Nihalani |
| 2012/0123478 A1 | 5/2012 | Winslow et al. |
| 2012/0150230 A1 | 6/2012 | Felix et al. |
| 2012/0226316 A1 | 9/2012 | Dant et al. |
| 2012/0253400 A1 | 10/2012 | Clark et al. |
| 2012/0253401 A1 | 10/2012 | Clark et al. |
| 2012/0253402 A1 | 10/2012 | McLean |
| 2012/0277806 A1 | 11/2012 | Smith et al. |
| 2012/0283778 A1 | 11/2012 | Yeh |
| 2013/0023932 A1 | 1/2013 | Helgerson |
| 2013/0103092 A1 | 4/2013 | Ballard |
| 2013/0172934 A1 | 7/2013 | Walker et al. |
| 2013/0184759 A1 | 7/2013 | Rinehart et al. |
| 2013/0325069 A1 | 12/2013 | Pereiro de Lamo et al. |
| 2014/0012333 A1 | 1/2014 | Tornier et al. |
| 2014/0018866 A1 | 1/2014 | Jankovic et al. |
| 2014/0180338 A1 | 6/2014 | Triplett |

* cited by examiner

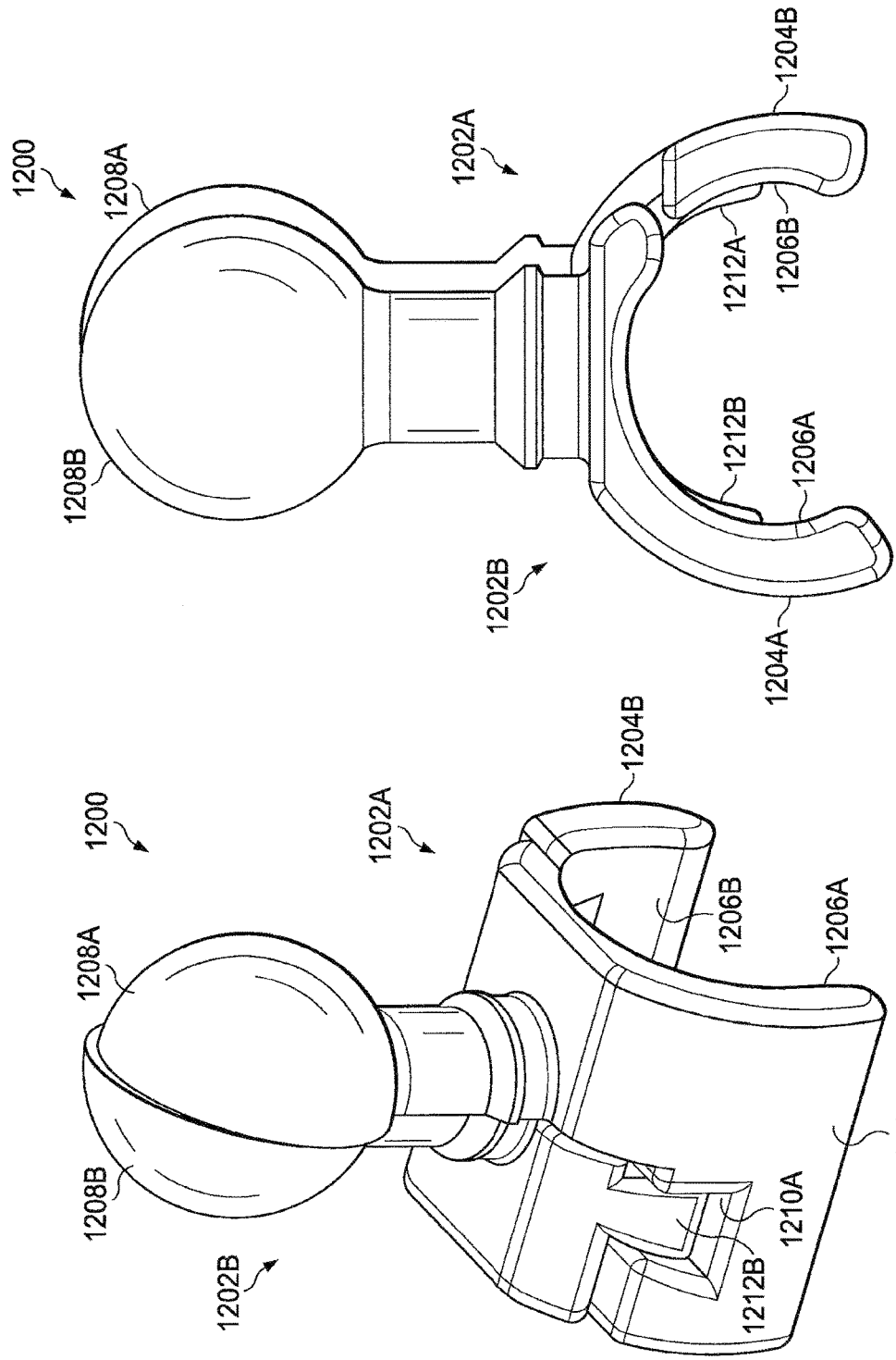

US 9,603,634 B1

PERCUTANEOUS ROD-TO-ROD CROSS CONNECTOR

This is a Continuation of patent application Ser. No. 14/941,135 filed Nov. 13, 2015.

FIELD OF THE INVENTION

The present disclosure relates to a minimally invasive surgical ("MIS") screw system comprising modular and/or pre-assembled rod-to-rod cross connectors and/or ipsilateral connectors for use with implantation rods, and related methods of using a MIS or traditional open screw system comprising modular and/or pre-assembled rod-to-rod cross connectors and/or ipsilateral connectors with implantation rods. In an embodiment, the system may allow true percutaneous delivery through the spinous ligament.

BACKGROUND OF THE INVENTION

The spinal column of bones is highly complex anatomical structure that includes over 20 bones coupled to one another, housing and protecting critical elements of the nervous system having innumerable peripheral nerves and circulatory bodies in close proximity. Despite its complexity, the spine is a highly flexible structure, capable of a high degree of curvature and twist in nearly every direction. The more than 20 discrete bones of an adult human spinal column are anatomically categorized as one of four classifications cervical, thoracic, lumbar, or sacral and are coupled together sequentially to one another by a tri-joint complex that consists of an anterior disc and two posterior facet joints. The anterior discs of adjacent bones are cushioned by cartilage spacers referred to as intervertebral discs or vertebrae. The cervical portion of the spine comprises the top of the spine up to the base of the skull and includes the first seven vertebrae. The intermediate 12 bones are thoracic vertebrae, and connect to the lower spine comprising the 5 lumbar vertebrae. The base of the spine comprises sacral bones, including the coccyx. With its complex nature, however, there is also an increased likelihood that surgery may be needed to correct one or more spinal pathologies.

Genetic or developmental irregularities, trauma, chronic stress, tumors and disease can result in spinal pathologies that either limit this range of motion or that threaten critical elements of the nervous system housed within the spinal column. A variety of systems have been disclosed in the art which achieve this immobilization by implanting artificial assemblies in or on the spinal column. These assemblies may be classified as anterior, posterior, or lateral implants. Lateral and anterior implants are generally coupled to the anterior position of the spine that is in the sequence of vertebral bodies. Posterior implants generally comprise pairs of rods, which are aligned along the axis that the bones are to be disposed, and that are then attached to the spinal column by hooks that couple to the lamina, hooks that attach to the transverse processes, or by screws that are inserted through pedicles. The orientation of each of these rods, however, are often limited by the alignment of the one or more screws they are affixed to.

Therefore, it is desirable, during surgical implantation of such posterior devices, to have a rod-to-rod cross connector or ipsilateral adjacent segment connector that allows for percutaneous delivery, independent alignment between pairs of rods and fastener screw, and improved reliability, durability, and ease of installment of said devices.

BRIEF SUMMARY

Disclosed herein is a surgical screw system comprising modular or pre-assembled rod-to-rod cross connectors or modular construct extensions for use with implantation rods, and related methods of using a surgical screw system comprising modular or pre-assembled rod-to-rod cross connectors with implantation rods. The surgical screw system allows for percutaneous delivery of the system. The system may comprise a rod attachment device having a split-orbital head at one end and a rod attachment claw at an opposite end, the rod attachment device. The rod attachment device may comprise a first claw portion comprising a first concave surface to engage with a surface of a rod, a first orbital head portion comprising a portion of a the split-orbital head, and a first pivoting mechanism disposed between the first claw portion and the first orbital head portion.

The rod attachment device may further comprise a second claw portion comprising a second concave surface to engage with an opposite surface of the rod from the first claw portion, a second orbital head portion comprising a portion of the split-orbital head, and a second pivoting mechanism disposed between the second claw position and the second orbital head position. The first and second claw portion s can be mated so that the first and second orbital head portions substantially align to form the split-orbital head, the first and second concave surfaces are aligned opposite each other, and the first and second pivoting mechanisms are aligned to pivot on a common axis, whereby when the first and second orbital head portions are placed in substantial circumferential alignment, the first and second concave surfaces are displaced towards each other.

The system may further comprise a first u-shaped body having a proximal end and a distal end, wherein the proximal end is operable to receive the split-orbital head of the rod attachment device, and the distal end comprises a threaded inner surface and is operable to receive a cross-connecting rod in a rod receiving channel.

The system may further comprise a retaining ring having a conical shape adapted to be mounted within the proximal end of the u-shaped body, wherein an interior surface of the retaining ring is adapted to be mated with a proximal end of the split orbital head.

The system may further comprise a pressure cap having a proximal end with a surface adapted to mate with a distal end of the split orbital head of the attachment device and a distal end with a u-shaped surface adapted to receive a cross-connecting rod, wherein the pressure cap is adapted to be slidably attached within the first u-shaped body such that the u-shaped surface is substantially aligned with the first u-shaped body.

The system may further comprise a compression element having a threaded portion adapted to engage with the threaded inner surface of the u-shaped body so that the compression element can be driven adjacent to and against the cross-connecting rod, whereby when the compression element is driven against the cross connecting rod, the cross-connecting rod is driven against the pressure cap, thereby driving the split orbital head against the conical retaining ring, thus bringing the split orbital head into substantial circumferential alignment.

BRIEF DESCRIPTION OF THE DRAWINGS

Embodiments are illustrated by way of example in the accompanying figures, in which like reference numbers indicate similar parts, and in which:

FIG. 12 depicts an elevation view of a sliding modular split-orbital rod connector, in accordance with one embodiment of the present disclosure;

FIG. 13 depicts a side view of the sliding modular split-orbital rod connector of FIG. 12, in accordance with one embodiment of the present disclosure;

DETAILED DESCRIPTION

For purposes of describing and claiming the present disclosure, the term "interference fit" is intended to refer to physical contact between two or more components and may include a slip fit, a ball-joint fit, or similar fit between two or more components. In addition, the terms "modular" and "modularity" are intended to refer to the interactions between the various components of the rod-to-rod cross connecting system described herein. Various combinations of individual components may come pre-assembled together, or each component may be assembled together component-by-component during surgery.

Figure 1:
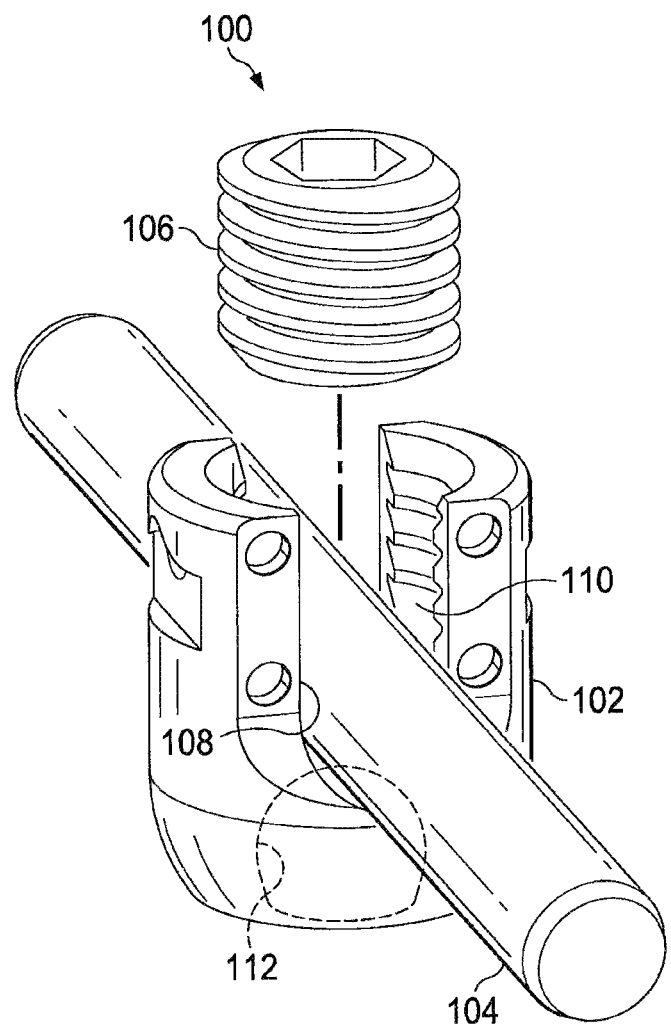
FIG. 1 depicts a prior art system for connecting a fastener element (e.g., a pedicle screw) relative to a rod for vertebral fixation.

FIG. 1 depicts a prior rut connection system 100 for connecting a fastener element (e.g., a pedicle screw, not shown) relative to a rod 104 for vertebral fixation. Connection system 100 may comprise a U-shaped body 102, the rod 104, and a compression element 106. The rod 104 may be shaped to fit within the U-shaped body 102 at a rod receiving channel 108 with a slip fit. After the rod 104 is received within the rod receiving channel 108, the compression element 106 may be threaded into the U-shaped body 102 and mate with internal threads 110 of the U-shaped body 102. The compression element 106 may clamp the rod 104 against an orbital head of the fastener element when the fastener element is received into an orbital recess 112 of the U-shaped body 102. The U-shaped body 102 may be operable to rotate about the orbital head of the fastener element received into the orbital recess 112 in order to allow multi-axial rotation of the rod 104 relative to the fastener element. The fastener element and the U-shaped body 102 may comprise separate components or may comprise a single component wherein the fastener element is operable to rotate independently of the U-shaped body 102.

Figure 2:
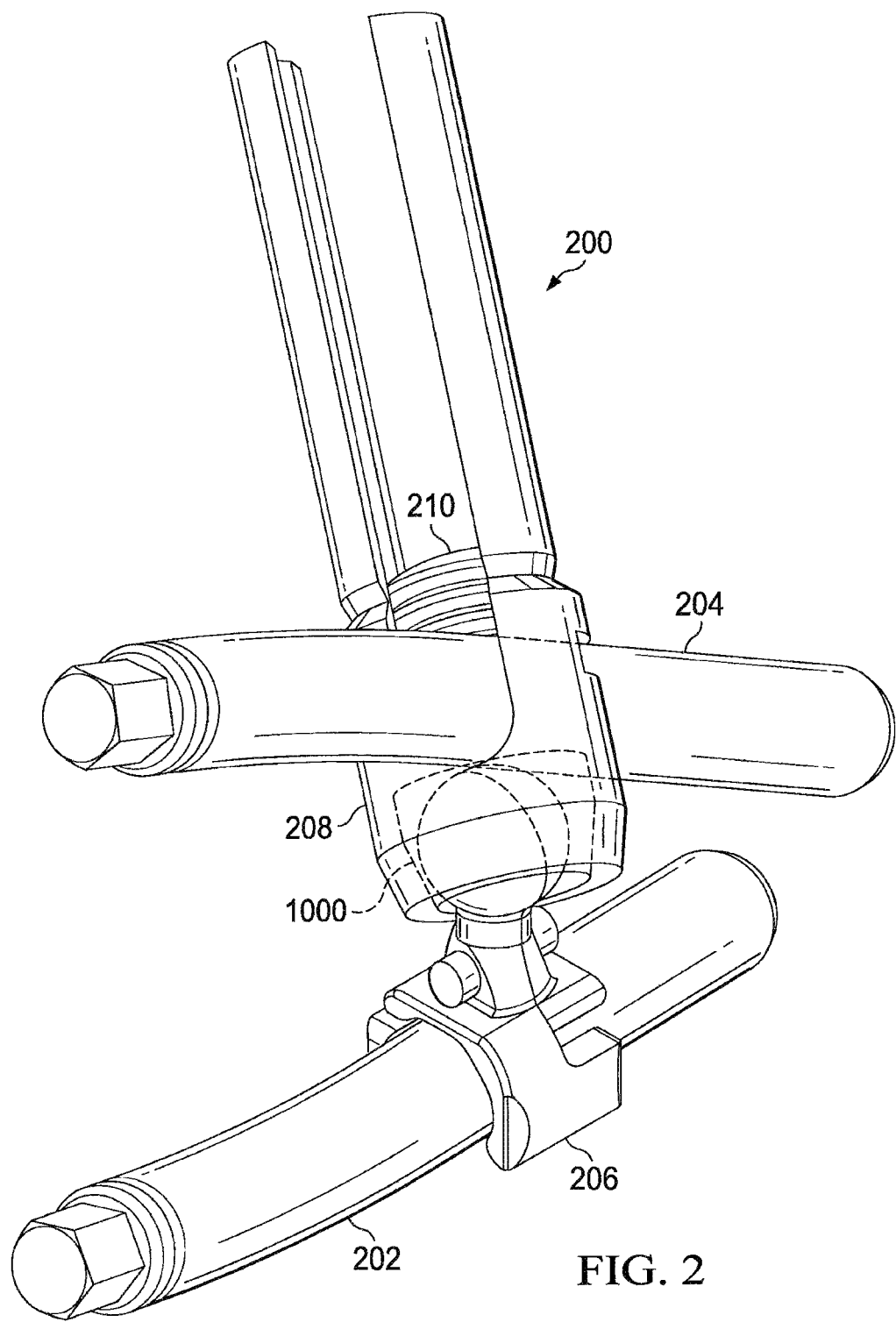
FIG. 2 depicts an elevation view of a modular rod-to-rod cross connecting system for percutaneous delivery, in accordance with one embodiment of the present disclosure.

FIG. 2 depicts an elevation view of a modular rod-to-rod cross connecting system 200 for percutaneous delivery, in accordance with one embodiment of the present disclosure. The modular rod-to-rod cross connecting system 200 may comprise a first rod 202, a second rod 204, a rod attachment device 206, a frangible U-shaped body 208, a compression element 210, a pressure cap (not shown), and a retaining ring (not shown). Each of the components of the modular rod-to-rod cross connecting system 200 will be described in more detail in relation to corresponding FIGS. 3-11.

Figure 3:
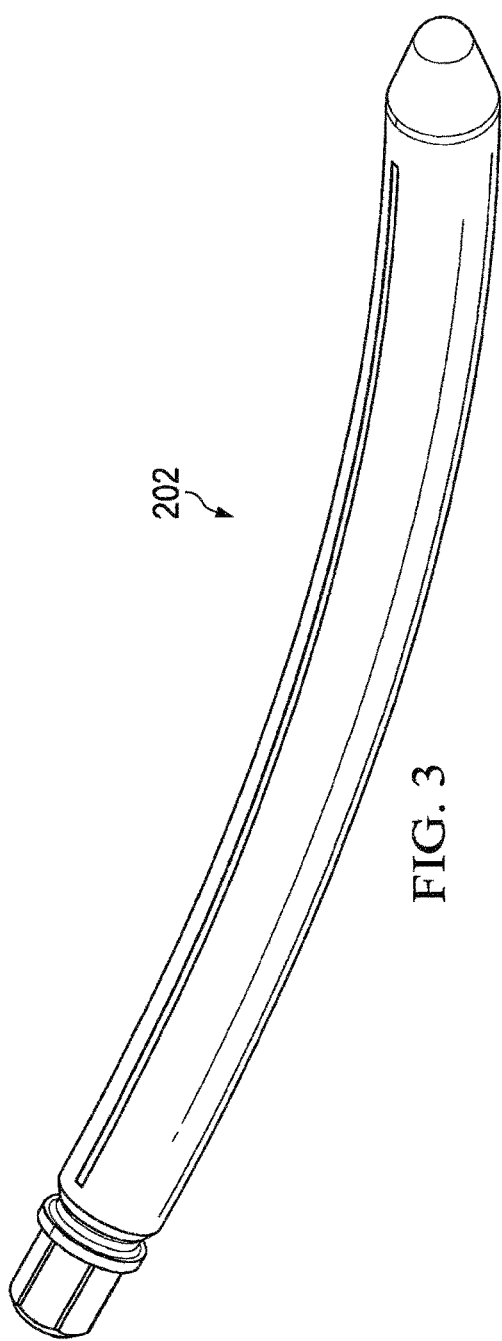
FIG. 3 depicts an elevation view of a first rod of the modular rod-to-rod cross connecting system of FIG. 2, in accordance with one embodiment of the present disclosure.
Figure 4:
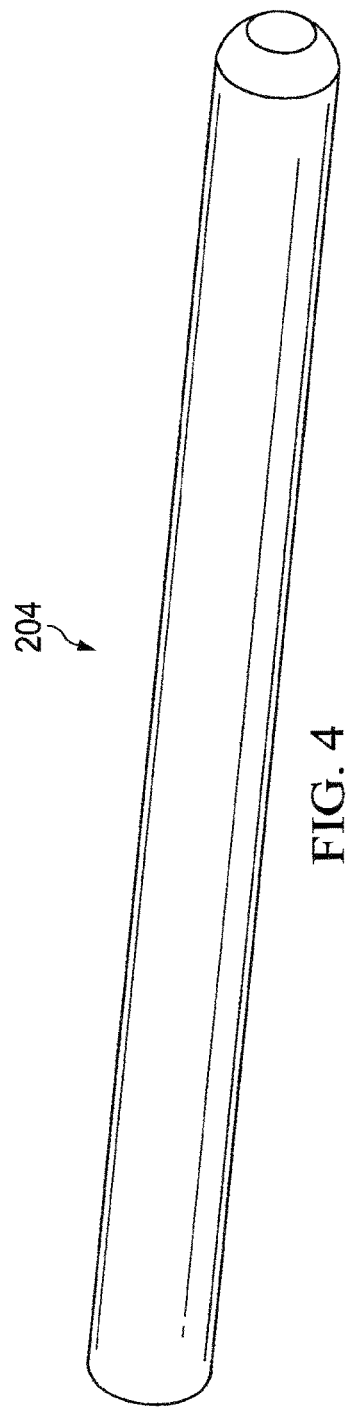
FIG. 4 depicts an elevation view of a second rod of the modular rod-to-rod cross connecting system of FIG. 2, in accordance with one embodiment of the present disclosure.

FIG. 3 depicts an elevation view of the first rod 202 and FIG. 4 depicts an elevation view of the second rod 204. The first and second rods 202, 204 may be any standard rod used in cervical, thoracic, or lumbar applications or sacral or iliac fixation. In one embodiment, the first and second rods 202, 204 may be placed parallel to or perpendicular to a spinal construct. In an embodiment, the first and second rods 202, 204 may be the same diameter or different diameters. For example, the first rod 202 may be a 5.5 mm diameter rod while the second rod 204 may a 3.5 mm diameter rod in an embodiment. The first and second rods 202, 204 may be any diameter between approximately 3.0 to approximately 6.0 mm. The length of the rods may be determined by the desired application of the modular rod-to-rod cross connector system. The rods 202, 204 may be curved, sigmoidal, or straight and may comprise rounded, squared, or tapered ends, as required each specific application. Advantageously, the disclosed embodiments allow for percutaneous and/or 'open' delivery of the modular rod-to-rod cross connector system. However, in addition to the rod-to-rod cross linking described in the disclosed embodiments, the first and second rods 202, 204 may be used to attach a construct to an adjacent ipsilateral level and/or as an offset connector within the same construct, for example for adjacent segment and/or iliac fixation.

Figure 6:
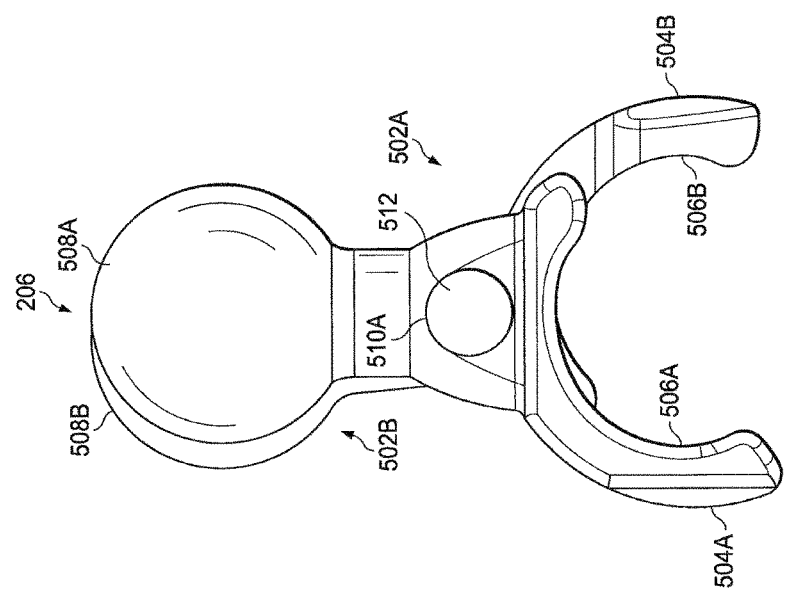
FIG. 6 depicts a side view of the pivoting modular split-orbital rod connector of FIG. 5, in accordance with one embodiment of the present disclosure.
Figure 5:
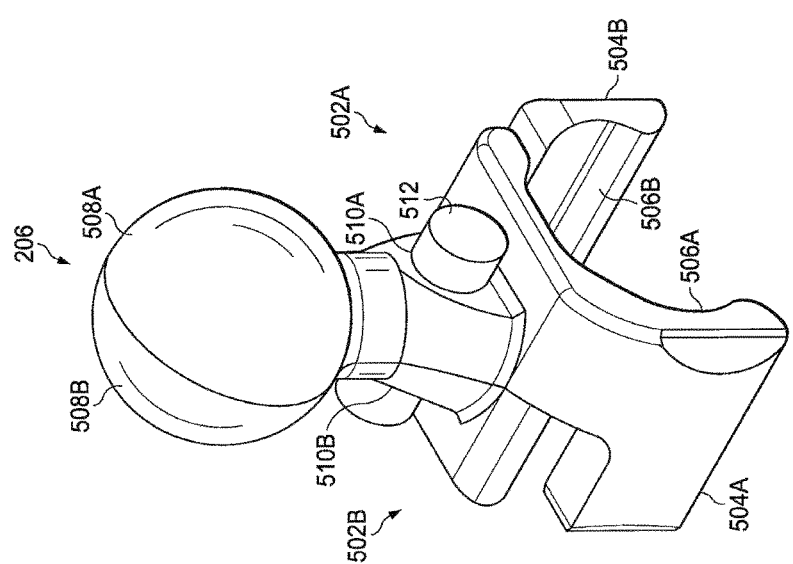
FIG. 5 depicts an elevation view of a pivoting modular split-orbital rod connector of the modular rod-to-rod cross connecting system of FIG. 2, in accordance with one embodiment of the present disclosure.

FIG. 5 depicts an elevation view and FIG. 6 depicts a side view of the pivoting modular split-orbital head rod attachment device 206 of the modular rod-to-rod cross connecting system of FIG. 2, in accordance with one embodiment of the present disclosure. The rod attachment device 206 may comprise a first portion 502A pivotably mated with a second portion 502B.

The first portion 502A may comprise a first claw portion 504A comprising a first concave surface 506A operable to engage with a surface of a rod (not shown) such as the first rod 202 depicted in FIG. 2. The first claw portion 504A may be located at a proximal end of the first portion 502A. The first portion 502A may further comprise a first orbital head 508A comprising a portion of the split-orbital head. The first orbital head 508A may be located at a distal end of the first portion 502A. The first portion 502A may further comprise a first pivoting mechanism 510A disposed between the first claw portion 504A and the first orbital head portion 508A. In an embodiment, the first pivoting mechanism 510A may be an aperture operable to receive and mate with a pivot pin 512.

The second portion 502B may comprise a second claw portion 504B comprising a second concave surface 506B operable to engage with a surface of a rod (not shown) such as the first rod 204 depicted in FIG. 2. The second claw portion 504B may be located at a proximal end of the second portion 502B. The second portion 502B may further comprise a second orbital head 508B comprising a portion of the split-orbital head. The second orbital head 508B may be located at a distal end of the second portion 502B. The second portion 502B may further comprise a second pivoting mechanism 510B disposed between the second claw portion 504B and the second orbital head portion 508B. In an embodiment, the second pivoting mechanism 510B may be an aperture operable to receive and mate with the pivot pin 512.

The first and second portions 502A, 502B may each further comprise flat surfaces operable to interact with each other when the first and second portions 502A, 502B are mated together with the pivot pin 512. The first and second portions 502A, 502B may align with each other along a common axis formed through the first and second pivoting mechanisms 510A, 510B, and when the pivot pin 512 is received through the first and second pivoting mechanisms 510A, 510B, the first and second concave surfaces 506A, 506B may be aligned opposite each other and the first and second orbital head portions 508A, 508B may be aligned proximate to each other.

When the first and second orbital head portions 508A, 508B are not in circumferential alignment, as shown in FIG. 6, the first and second concave surfaces 506A, 506B may be displaced away from each other, allowing a rod, such as the first rod 204 depicted in FIG. 2, to be received within and between the first and second claw portions 504A, 504B of the split-orbital rod connector 206.

When the first and second orbital head portions 508A, 508B are placed in substantial circumferential alignment to form the split-orbital head, as shown in FIG. 5, the split-orbital head may be received within an orbital recess of the U-shaped body 208 of FIG. 2, and the first and second concave surfaces 506A, 506B may be displaced toward each other and around a rod, such as the first rod 204 depicted in FIG. 2, thereby preventing the rod from moving relative to the split-orbital rod connector 206.

Figure 7:
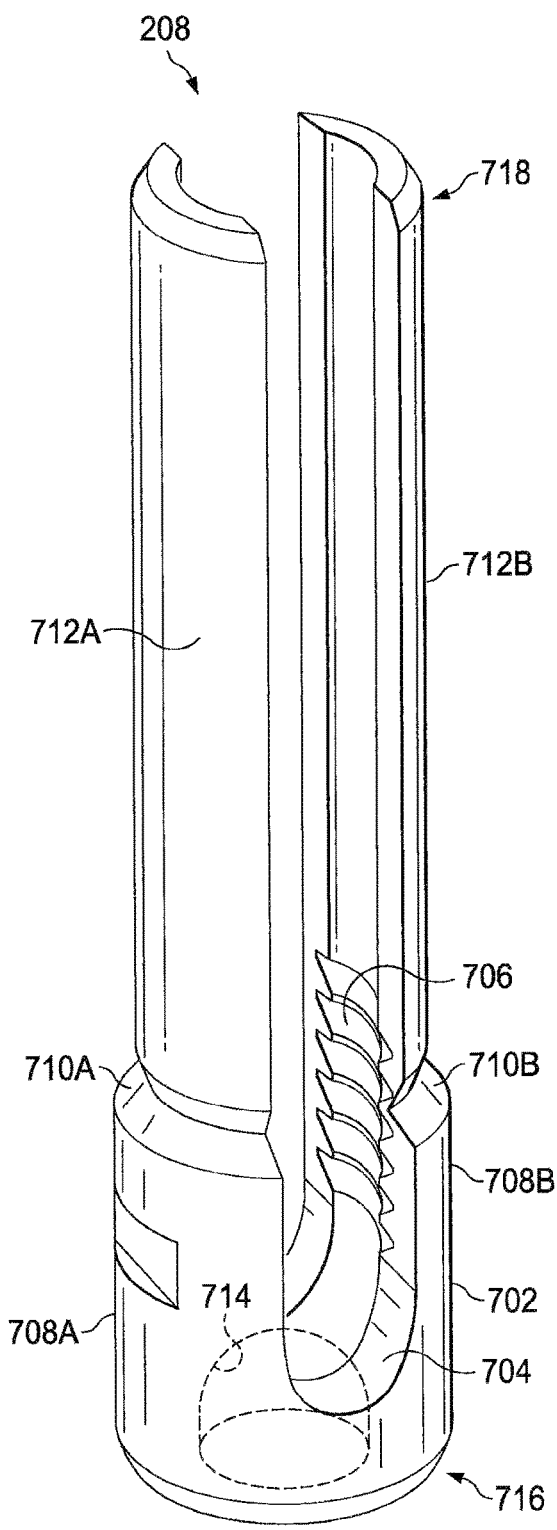
FIG. 7 depicts an elevation view of a frangible U-shaped body of the modular rod-to-rod cross connecting system of FIG. 2, in accordance with one embodiment of the present disclosure.

FIG. 7 depicts an elevation view of the frangible U-shaped body 208 of the modular rod-to-rod cross connecting system of FIG. 2, in accordance with one embodiment of the present disclosure. The U-shaped body 208 may comprise a body 702 comprising a rod receiving channel 704, a first body side 708A, and a second body side 708B. The rod receiving channel 704 may be located at a distal end 718 and may define the first and second body sides 708A, 708B. The first and second body sides 708A, 708B may comprise internal threads 706 located proximate to the rod receiving channel 704 and configured to receive the second rod 202, as shown in FIG. 2, and a non-modular compression element, as described in more detail in relation to FIG. 8.

The body 702 may further comprise an internal recess 714 proximate to a proximal end 716 and opposite the rod receiving channel 704. The internal recess 714 may be operable to receive the split-orbital head of the rod attachment device 206, as shown in FIG. 2, and a retaining ling. The U-shaped body 208 may be operable to rotate about the split-orbital head of the rod attachment device (not shown) when received into the recess 714 in order to allow multi-axial rotation of the body 702 and the second rod 202 (not shown) relative to the rod attachment device 206 and the first rod 204 (not shown).

The U-shaped body 208 may further comprise first and second removable rums 712A, 712B operable to be removed from the body 702 at creases 710A, 710B. The first and second removable arms 712A, 712B may be located proximate to the distal end 718.

Figure 8:
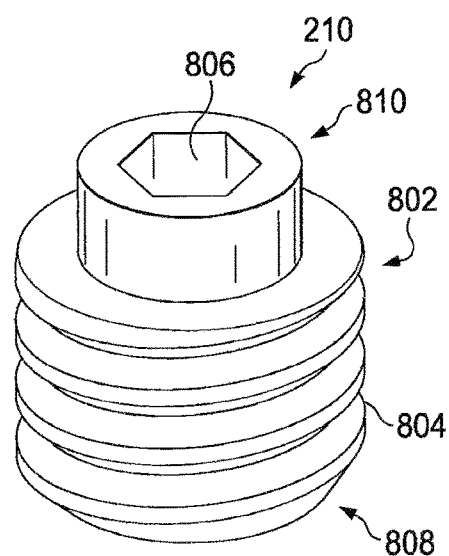
FIG. 8 depicts an elevation view of a compression element of the modular rod to-rod cross connecting system of FIG. 2, in accordance with one embodiment of the present disclosure.

FIG. 8 depicts an elevation view of a compression element 210, in accordance with one embodiment of the present diclosure. The compression element 210 may comprise a compression element body 802 comprising a proximal end 808 and a distal end 810. Part or all of the compression element body 802 may comprise threads 804 about the compression element body 802. The threads 804 may allow the non-modular compression element 210 to mate with the threads of the first and second body sides of the U-shaped body shown in FIG. 7.

The distal end 810 of the non-modular compression element 210 may further comprise a driving recess 806 operable to receive a driving instrument (not shown). Although shown as a square-shaped driving recesses 806 in FIG. 8, the driving recess 806 may be a hex-shaped, Philips-head shaped, flathead-shaped, or any other shape operable to receive a driving instrument.

Figure 9:
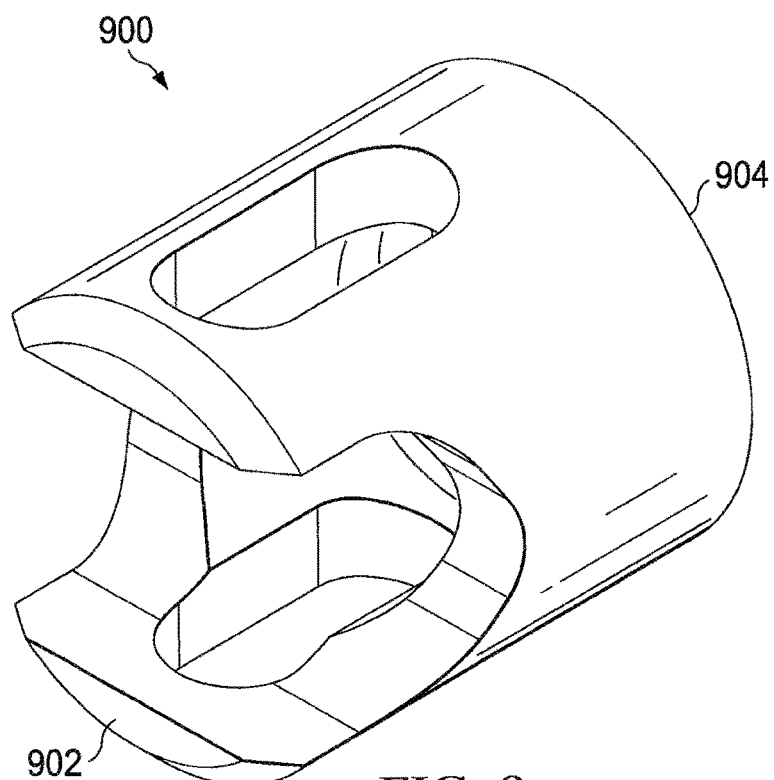
FIG. 9 depicts an elevation view of a pressure cap of the modular rod-to-rod cross connecting system of FIG. 2, in accordance with one embodiment of the present disclosure.

FIG. 9 depicts an elevation view of a pressure cap 900 of the modular rod-to-rod cross connecting system of FIG. 2, in accordance with one embodiment of the present disclosure. The pressure cap 900 may comprise a distal indention 902 located at a distal end operable to interact with a rod and a proximal indention 904 operable to interact with an orbital head.

In an embodiment, a retaining ring may be used instead of the pressure cap 900. In an embodiment, the retaining ring may be an arcuate member having a radius of at least 120°, thereby allowing a user to independently set the orientations of first and second rods.

Figure 10:
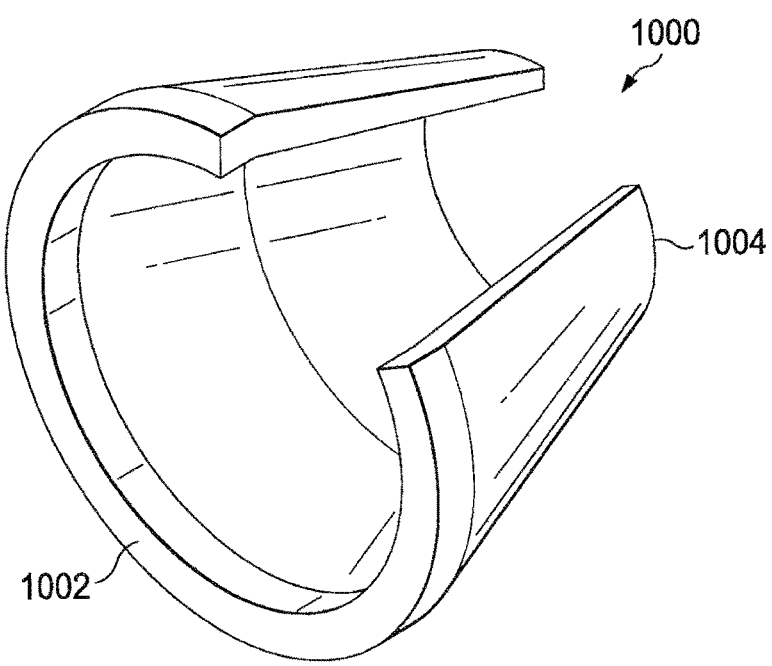
FIG. 10 depicts an elevation view of a retaining ring of the modular rod-to-rod cross connecting system of FIG. 2, in accordance with one embodiment of the present disclosure.

FIG. 10 depicts an elevation view of a retaining ring 1000 of the modular rod-to-rod cross connecting system of FIG. 2, in accordance with one embodiment of the present disclosure. The retaining ring 1000 may be a tapered retaining ring such that a diameter of the distal end 1002 is greater than a diameter of the proximal end 1004. The retaining ring 1000 may be received within the internal recess 714 of the U-shaped body 208 depicted in FIG. 7 and may be operable to push the sides of the split ball head together. Because of the frusto conical shape of the retaining ring 1000, once the split ball head is received through proximal (smaller) end 1004, the split ball head is operable to open and close around a rod, but the split ball head cannot be easily removed from the retaining ring 1000. In an embodiment, the retaining ring 1000 may be a solid ring or may comprise an opening. In an embodiment, the opening may be about a 60° opening about the outer circumference of the retaining ring 1000, as measured from the center of the retaining ring 1000. In an embodiment, the retaining ring may be approximately 0.030" thick.

Figure 11:
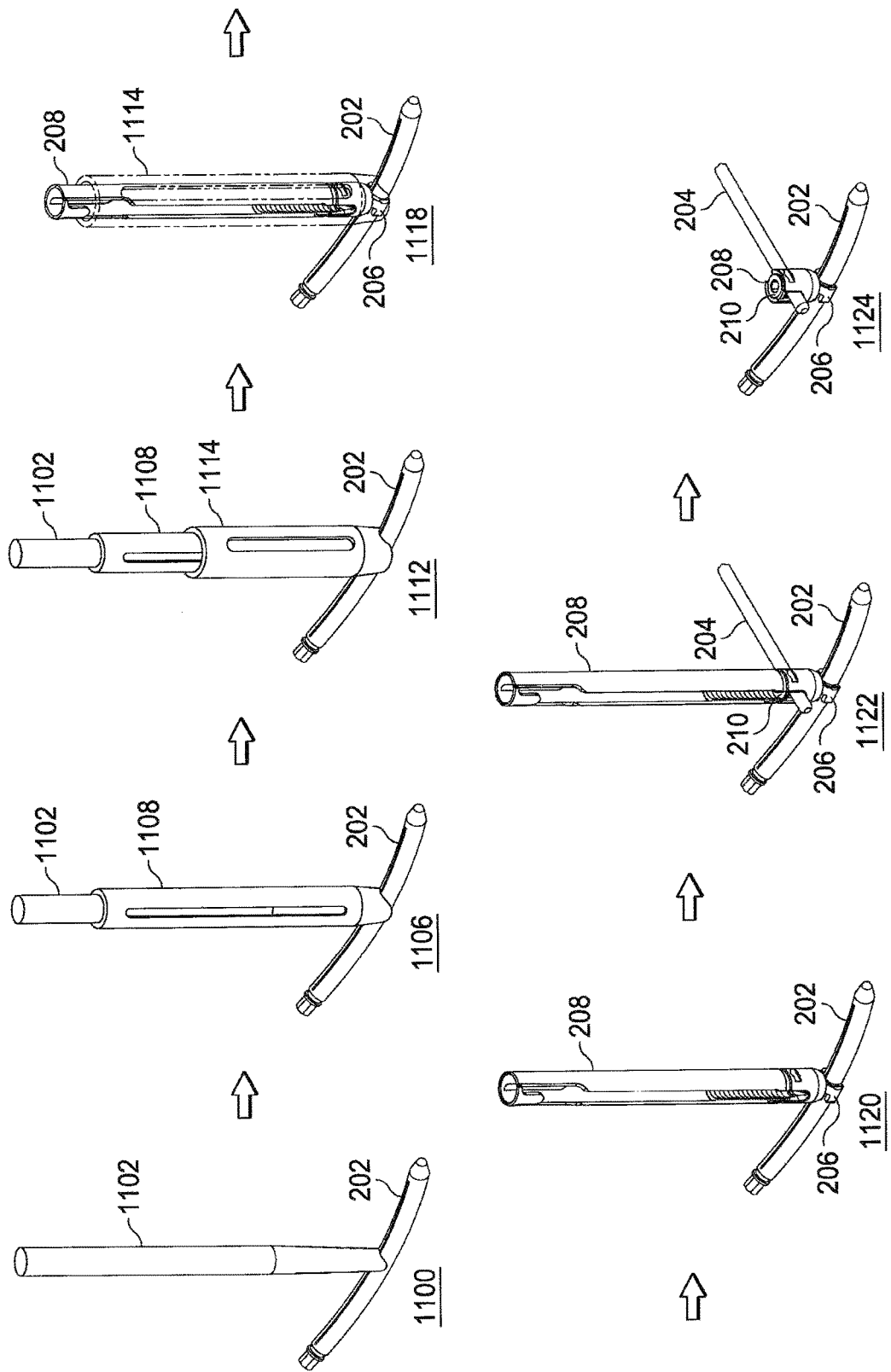
FIG. 11 depicts a surgical flow diagram for inserting an implant of the modular rod-to-rod cross connecting system of FIG. 2, in accordance with one embodiment of the present disclosure.

FIG. 11 depicts a surgical flow diagram for inserting an implant of the modular rod-to-rod cross connecting system of FIG. 2, in accordance with one embodiment of the present disclosure. In operation, the first rod 204 may already be received and secured within the patient or the first rod 204 may be approximately positioned but not secured within the patient.

At step 1100, a first dilator 1102 may be inserted into the patient and a proximal end 1104 of the first dilator 1102 may interact with a surface of the first rod 202. The first dilator 1102 may be a hollow or solid dilator, it may be cannulated to receive a K-wire, and in an embodiment, the first dilator 1102 may be between approximately 6 and 8 mm in diameter.

At step 1106, a second dilator 1108 may be received around the first dilator 1102 and a proximal end 1110 of the second dilator 1108 may interact with a surface of the first rod 202. The second dilator 1108 may be a hollow dilator, and in an embodiment, the second dilator 1108 may be approximately 11 mm in diameter.

At step 1112, a third dilator 1114 may be received around the first dilator 1102 and the second dilator 1108 and a proximal end 1116 of the third dilator 1114 may interact with a surface of the first rod 202. The third dilator 1114 may be a hollow dilator, and in an embodiment, the third dilator 1114 may be approximately 14 mm in diameter.

At step 1118, the first dilator 1102 and the second dilator 1108 are removed from within the third dilator 1114. Next, the pivoting modular split-orbital rod connector 206 is inserted into the hollow third dilator 1114 and the pivoting modular split-orbital rod connector 206 is received around the first rod 202. Before the U-shaped body 208 is received within the third dilator 1114, the first and second claw portions 504A, 504B may pivot outwardly, as shown in FIG. 6, wherein the first and second claw portions 504A, 504B may be received around the first rod 202. After the pivoting modular split-orbital rod connector 206 is received around the first rod 202, the U-shaped body 208 is inserted into the third dilator 1114.

Before the U-shaped body 208 is snapped onto the pivoting modular split-orbital rod connector 206 (or the U-shaped body 208 and the pivoting modular split-orbital rod connector 206 may be pre-assembled as one piece prior to fastening to the first rod 202), the snug interference fit between the pivoting modular split-orbital rod connector 206 and the first rod 202 allows minor displacement of the first rod 202 slidably along its axis relative to the pivoting modular split-orbital rod connector 206. After the desired orientation and/or placement of the first rod 202 has been achieved, the U-shaped body 208 may be placed or "snapped" over the first and second orbital head portions 508A, 508B of the pivoting modular split-orbital rod connector 206, pivoting the first and second orbital head portions 508A, 508B to substantially align to form the split-orbital head and the first and second concave surfaces 506A, 506B to surround the first rod 204 such that minor adjustments to the first rod 204 are no longer possible.

At step 1120, the third dilator is removed from around the U-shaped body 208, thereby allowing the second rod (not shown) to be connected to the first rod 202 with the pivoting modular split-orbital rod connector 206.

At step 1122, the second rod 204 may be inserted into the rod receiving channel of the U-shaped body 208. The second rod 204 may be rotated relative to the first rod 202 and the pivoting modular split-orbital rod connector 206 and may slide relative to the pivoting modular split-orbital rod connector 206. The interference fit between the pivoting modular split-orbital rod connector 206 and the U-shaped body 208 may be a ball-joint fit that allows the U-shaped body 208 and the first rod 202 to pivot about the split-orbital head of the pivoting modular split-orbital rod connector 206 so that the second rod 204 may be aligned in a second orientation independent of the first orientation of the first rod 202. In an embodiment, the second U-shaped body 208 may be circumferentially pivotable on the split-orbital head of the pivoting modular split-orbital rod connector 206 around a longitudinal axis defined from the proximal end to the distal end of the pivoting modular split-orbital rod connector 206 and/or may have a desired degree of angular freedom (e.g., approximately 26° from the longitudinal axis of the modular compression element 206 or 52° from one side to the other).

After the second orientation of the second rod 204 is set as approximately desired, the compression element 210 may be operable to be inserted into the rod receiving channel of the U-shaped body 208. The compression element 210 may be operable to be driven down onto the second rod 204 with a driving element (not shown). The threads 804 of the compression element 210 may be operable mate with the internal threads 706 of the first and second body sides 708A, 708B of the U-shaped body 208, allowing the second rod 204 to be operable to be driven against an end of the rod receiving channel 704. When the second rod 202 has been driven adjacent to the end of the rod receiving channel 704, the distal end of the compression element 210 may be in an interference fit with a first surface of the second rod 204 and a second surface of the second rod 204 may be in an interference fit with a surface of the split-orbital head of the pivoting modular split-orbital rod connector 206.

Before the compression element 210 is fully driven down onto the second rod 204, the snug interference fit between the compression element 210 and the second rod 204 and between the second rod 204 and the split-orbital head of the pivoting modular split-orbital rod connector 206 may be a slip fit that allows minor displacement of the second rod 204 along its axis relative to the U-shaped body 208 and may allow the second rod 204 and the U-shaped body 208 minor pivotable adjustment relative to the compression element 210 when setting the second orientation of the second rod 204. After the desired second orientation of the second rod 204 has been achieved, the compression element 210 may be further driven against the second rod 204 so that the second orientation of the second rod 204 is set. Then, minor adjustments of second orientation of the second rod 204 are no longer possible. Advantageously, the orientation s of the first rod 202 and the second rod 204 may be set independently of each other.

At step 1124, and after the driving element (not shown) has been removed, the first and second removable arms may be detached from the U-shaped body 208 at the first and second creases. At this point, the orientations of the first rod 202 and the second rod 204 may be secured relative to each other.

As discussed with respect to the individual elements and the surgical process described in relation to FIGS. 2-11, above, the rod attachment device 206 may lock around the second rod 204 via one of two methods. First, the rod attachment device 206 may lock around the second rod 204 when the retaining ring 1000 inside the body 700 of the frangible U-shaped body 208 acts to push the first and second orbital heads 508A, 508B of the split-orbital rod connector 206 together, locking the first and second claw portions 504A, 504B around the second rod 204. Second, one or more of the dilators discussed in the surgical method described in relation to FIG. 11 may engage with the rod attachment device 206 at the first and second claw portions 504A, 504B, compressing the first and second claw portions 504A, 504B together and closing the first and second claw portions 504A, 504B around the second rod 204.

FIG. 12 depicts an elevation view of a sliding modular split-orbital rod connector 1200, in accordance with one embodiment of the present disclosure. FIG. 13 depicts a side view of the sliding modular split-orbital rod connector 1200 of FIG. 12, in accordance with one embodiment of the present disclosure. Similar to the modular split-orbital rod attachment device 206 of the modular rod-to-rod cross connecting system of FIGS. 5-6, the sliding modular split-orbital rod connector 1200 may comprise a first portion 1202A slidably mated with a second portion 1202B.

The first portion 1202A may comprise a first claw portion 1204A comprising a first concave surface 1206A operable to engage with a surface of a rod (not shown) such as the first rod 202 depicted in FIG. 2. The first claw portion 1204A may be located at a proximal end of the first portion 1202A. The first portion 1202A may further comprise a first orbital head 1208A comprising a portion of the split-orbital head. The first orbital head 1208A may be located at a distal end of the first portion 1202A.

The second portion 1202B may comprise a second claw portion 1204B comprising a second concave surface 1206B operable to engage with a surface of a rod (not shown) such as the first rod 202 depicted in FIG. 2. The second claw portion 1204B may be located at a proximal end of the second portion 1202B. The second portion 1202B may further comprise a second orbital head 1208B comprising a portion of the split-orbital head. The second orbital head 1208B may be located at a distal end of the second portion 1202B.

The sliding modular split-orbital rod connector 1200 may further comprise a tongue and groove system to allow the first and second portions 1202A, 1202B to slide relative to each other wherein the first and second orbital heads 1208A, 1208B may substantially align with each other or may be spaced apart from each other. The first portion 1202A may comprise a first groove 1210A located in the first claw portion 1204A and a first tongue 1212A located opposite and offset from the first groove 1210A in the first claw portion 1204A operable to receive and mate with a second tongue. The second portion 1202B may comprise a second groove 1210B located in the second claw portion 1204B and a second tongue 1212B located opposite and offset from the second groove 1210B in the second claw portion 1204B. In an embodiment, the first groove 1210A is operable to receive the second tongue 1212B and the second groove 1210B is operable to receive the first tongue 1212A.

The first and second portions 1202A, 1202B may each further comprise flat surfaces operable to interact with each other when the first and second portions 1202A, 1202B are mated together with the tongue and groove system. The first and second portions 1202A, 1202B may align with each other along a common axis. The first and second portions 1202A, 1202B may slide along the flat surfaces and the common axis such that the when the first and second orbital heads 1208A, 1208B are aligned, the first and second claw portions 1204A, 1204B are proximate to teach other and operable to clamp around a rod. Conversely, when the first and second orbital heads 1208A, 1208B are spaced apart from each other such that they do not align, the first and second claw portion s 1204A, 1204B are also spaced apart from each other and operable to receive a rod.

When the first and second orbital head portions 1208A, 1208B are not in circumferential alignment, as shown in FIG. 13, the first and second concave surfaces 1206A, 1206B may be displaced away from each other, allowing a rod, such as the first rod 202 depicted in FIG. 2, to be received within and between the first and second claw portions 1204A, 1204B of the sliding modular split-orbital rod connector 1200.

When the first and second orbital head portions 1208A, 1208B are placed in substantial circumferential alignment to form the split-orbital head (not shown), the split-orbital head may be received within an orbital recess of the U-shaped body 208 of FIG. 2, and the first and second concave surfaces 1206A, 1206B may be displaced toward each other and around a rod, such as the first rod 202 depicted in FIG. 2, thereby preventing the rod from moving relative to the sliding modular split-orbital rod connector 1200.

The sliding modular split-orbital rod connector 1200 of FIGS. 12-13 may similarly be used in the surgical flow diagram for inserting an implant of the modular rod-to-rod cross connecting system depicted in FIG. 11, with the sliding modular split-orbital rod connector 1200 replacing the pivoting split-orbital rod connector 206.

In addition, sliding modular split-orbital rod connector 1200 may similarly lock around the second rod 204 via one of two methods. First, the sliding modular split-orbital rod connector 1200 may lock around the second rod 204 when the retaining ring 1000 inside the body 700 of the frangible U-shaped body 208 acts to slide the first and second orbital heads 1208A, 1208B of the sliding modular split-orbital rod connector 1200 together, locking the first and second claw portion s 1204A, 204B around the second rod 204. Second, one or more of the dilators discussed in the surgical method described in relation to FIG. 11 may engage with the sliding modular split-orbital rod connector 1200 at the first and second claw portions 1204A, 1204B, sliding and compressing the first and second claw portions 1204A, 1204B together and closing the first and second claw portions 1204A, 1204B around the second rod 204.

Figure 14:
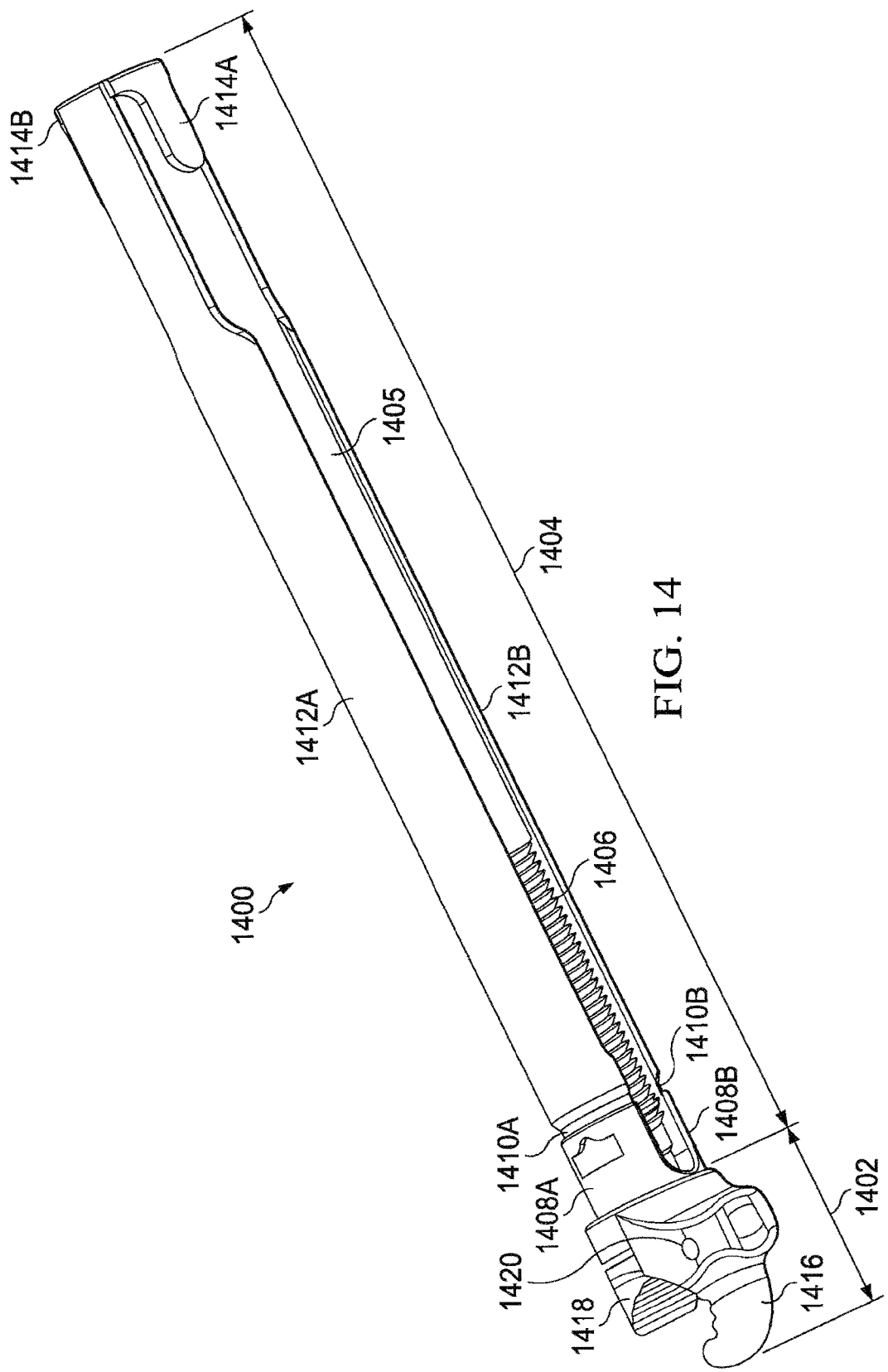
FIG. 14 depicts an elevation view of an offset jaw rod connector, in accordance with one embodiment of the present disclosure.
Figure 15:
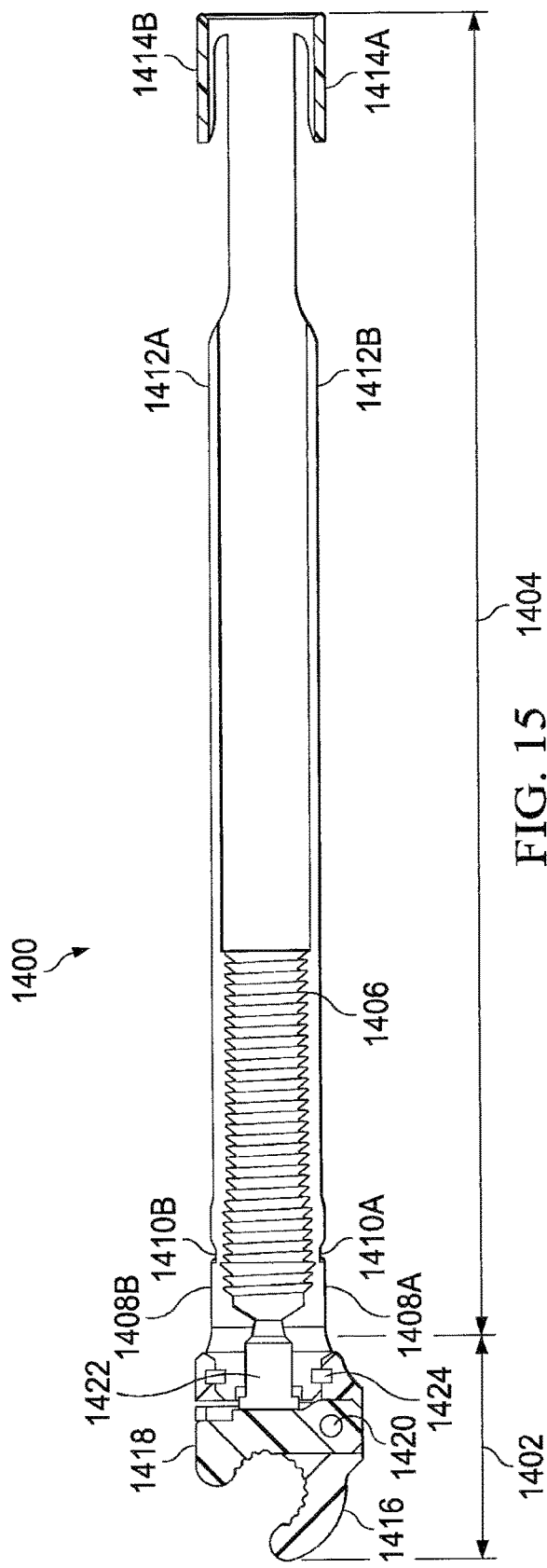
FIG. 15 depicts a side view of the offset jaw rod connector of FIG. 14, in accordance with one embodiment of the present disclosure.

FIG. 14 depicts an elevation view of an offset jaw rod connector 1400, in accordance with one embodiment of the present disclosure. FIG. 15 depicts a side view of the offset jaw rod connector 1400 of FIG. 14, in accordance with one embodiment of the present disclosure. The offset jaw rod connector 1400 comprises a rod attachment device 1402 located at a proximal end and a U-shaped body 1404 located at a distal end. The rod attachment device 1402 comprises a first jaw portion 1416 and a second jaw portion 1418.

Figure 16:
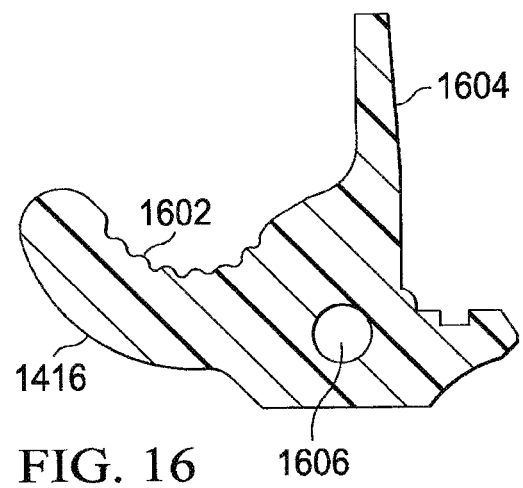
FIG. 16 depicts a side view of a first jaw portion of the offset jaw rod connector of FIG. 14, in accordance with one embodiment of the present disclosure.

FIG. 16 depicts a side view of the first jaw portion 1416 of the offset jaw rod connector 1400 of FIG. 14, in accordance with one embodiment of the present disclosure. The first jaw portion 1416 may comprise a first concave surface 1602 operable to engage with a surface of a rod such as the first rod 202 depicted in FIG. 2. The first concave surface 1602 of the first jaw portion 1416 may comprise an arc of approximately 60°, although the arc may range from approximately 40° to approximately 80°. The first jaw portion 1416 may further comprise a first pivoting mechanism 1606. In an embodiment, the first pivoting mechanism 1606 may be an aperture operable to receive a pivot pin. The first jaw portion 1416 may further comprise a first biasing member 1604. The first biasing member 1604 may be operable to be engaged with a surface of the second jaw portion 1418, as discussed below.

Figure 17:
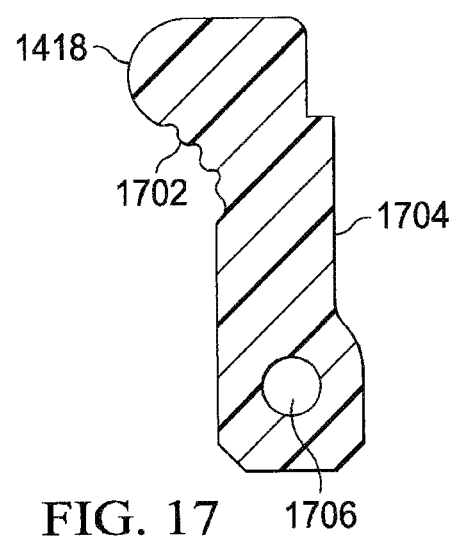
FIG. 17 depicts a side view of a second jaw portion of the offset jaw rod connector of FIG. 14, in accordance with one embodiment of the present disclosure.

FIG. 17 depicts a side view of a second jaw portion 1418 of the offset jaw rod connector 1400 of FIG. 14, in accordance with one embodiment of the present disclosure. The second jaw portion 1418 may comprise a second concave surface 1702 operable to engage with an opposite surface of the rod (not shown) from the first jaw portion 1416. The second concave surface 1702 of the second jaw portion 1418 may comprise an arc of approximately 150°, although the arc may range from approximately 120° to approximately 180°. The second jaw portion 1418 may further comprise a second pivoting mechanism 1706. In an embodiment, the second pivoting mechanism 1706 may be an aperture operable to receive a pivot pin. The second jaw portion 1716 may further comprise a second biasing surface 1704. The second biasing surface 1704 is operable to engage with the first biasing member 1604 of the first jaw portion 1416. The second pivoting mechanism 1706 may further comprise a second locking surface 1708 operable to interface with a pressure cap.

Together, the first and second concave surfaces 1602, 1702 of the first and second jaw portions 1416, 1418 may comprise an arc greater than approximately 180°, thereby allowing the first and second jaw portions 1416, 1418 to lock around a cross connecting rod.

In operation, the first jaw portion 1416 and the second jaw portion 1418 may be mated together when a pivot pin is received through the first and second pivoting mechanisms 1606, 1706. When the pivot pin is received through the first and second pivoting mechanisms, the first and second concave surfaces 1602, 1702 may be positioned on opposite sides of an opening operable to receive a rod. When inserting a rod into the opening formed by the first and second concave surfaces 1602, 1702, the second jaw portion 1418 may pivot distally (upwardly), creating a large enough opening to receive the rod therewithin. Once the rod is received within the opening, the first biasing member 1604 drives the second jaw portion 1418 proximally (downwardly) at the second biasing surface 1704, which drives the second jaw portion 1418 against the rod.

Referring back to FIGS. 14-15, the first U-shaped body 1404 of the offset jaw rod connector 1400 further comprises a proximal end proximate to the rod attachment device 1402 and a distal end opposite the proximal end. The proximal end may be pivotally and rotationally attached to the rod attachment device 1402 and the distal end may comprise a threaded inner surface 1406 and is operable to receive a cross connecting rod such as the second rod 204 in a rod receiving channel 1405.

The U-shaped body 1404 may comprise a first body side 1408A and a second body side 1408B that define the rod receiving channel 1405. The rod receiving channel 1405 may extend from approximately the distal end to approximately the proximal end of the first U-shaped body and a rod may be inserted into the rod receiving channel 1405 anywhere along the channel. The first and second body sides 1408A, 1408B may comprise internal threads 1406 located proximate to the rod receiving channel 1405 and configured to receive the second rod 204, as shown in FIG. 2, and a non-modular compression element, as described in more detail in relation to FIG. 8.

The U-shaped body 1404 may further comprise first and second removable arms 1412A, 1412B operable to be removed from the first and second body sides 1408A, 1408B at creases 1410A, 1410B. The first and second removable rums 1412A, 1412B may be located proximate to the distal end of the first and second body sides 1408A, 1408B. The internal threads 1406 may extend partially or fully within the first and second removable arms 1412A, 1412B.

The U-shaped body 1404 may further comprise first and second frangible tabs 1414A, 1414B. The first and second frangible tabs 1414A, 1414B may be located at a distal end of the U-shaped body 1404 and may connect the first and second removable rums 1412A, 1412B. In operation, after the orientation of the first and second rods have both been set relative to each other, the first and second frangible tabs 1414A, 1414B may be broken off from the first and second removable rums 1412A, 1412B and then the first and second removable rums 1412A 1412B may be splayed away from the first and second body sides 1408A, 1408B.

The offset jaw rod connector 1400 may further comprise a pressure cap 1422. The pressure cap may be the pressure cap depicted in FIG. 9 or may be sized and shaped specifically for the offset jaw rod connector 1400. The pressure cap 1422 may similarly comprise a U-shaped distal indention located at a distal end operable to interact with a rod and a proximal surface adapted to adjoin the second locking surface 1708 of the second jaw portion 1418.

The pressure cap 1422 may further comprise at least one chordal surface passing from the proximal end to the distal end. Similarly, the proximal end of the first U-shaped 1404 may comprise at least one chordal surface adapted to mate with the at least one chordal surface of the pressure cap 1422. The pressure cap 1422 may be adapted to be slidably attached within the first U-shaped body 1404 such that the U-shaped distal indention is substantially aligned with the first U-shaped body 1404, thereby preventing rotation of the pressure cap 1422 within the first U-shaped body 1404. The pressure cap 1422 may further comprise a proximal end comprising a proximal surface adapted to adjoin the second locking surface 1708 of the second jaw portion 1418.

The offset jaw rod connector 1400 may further comprise a retaining ring 1424. The retaining ring 1424 may be operable to be retained between a first annular recess defined in an inner surface of the first jaw portion 1416 and a second annular recess defined in an outer surface of the U-shaped body 1404. When the first jaw portion 1414 is pivotally attached to the first U-shaped body 1404, the retaining ring 1424 is mated with the first and second annular recesses. In an embodiment, the retaining ring 1424 may be an arcuate member having a radius of at least 120°, thereby allowing the rod attachment device 1402 to rotate relative to U-shaped body 1404, which allows a user to independently set the orientations of first and second rods.

In an embodiment, a pressure cap may be used in combination with the retaining ring 1424. The pressure cap may comprise a distal indention located at a distal end operable to interact with a rod and a proximal indention operable to interact with an orbital head.

The offset jaw rod connector 1400 may further comprise a compression element (not shown) such as the compression element 210 depicted in FIG. 8. The compression element may comprise a compression element body comprising a proximal end and a distal end. Part or all of the compression element body may comprise threads about the compression element body. The threads may allow the non-modular compression element to mate with the threads of the first and second body sides 1408A, 1408B of the first U-shaped body 1404.

The distal end of the non-modular compression element may further comprise a driving recess operable to receive a driving instrument (not shown). The driving recess 806 may be a hex-shaped, Philips-head shaped, flathead-shaped, or any other shape operable to receive a driving instrument.

In operation, when a first rod, such as first rod 202, is received within the opening between the first jaw portion 1416 and the second jaw portion 1418, and when a second rod, such as second rod 204, is received within the rod receiving channel 1405, the orientations of the first and second rods 202, 204 may be set independently of each other because of the rotation allowed by the retaining ring 1424. The compression element (not shown) may then be inserted into the first U-shaped body 1404 and threaded down the threaded inner surface until it is driven to and against the second rod 204. At this time, the orientations of the first and second rods 202, 204 may still be rotated independently of each other. When the compression element is driven firmly against a distal surface of the second rod 204, a proximal surface of the second rod 204 is driven against the distal surface of the pressure cap 1422, thereby driving the proximal surface of the pressure cap 1422 against the second locking surface of the second jaw portion 1418, rotating the second jaw portion 1418 downwardly and thus locking the second jaw portion 1418 against the first rod 202. When the compression element is firmly driven against the second rod, the orientations of both the first and second rods are locked relative to each other.

FIGS. 18-23, as discussed below, each depict additional rod-to-rod connectors that may be used to lock onto a first, proximal rod, such as first rod 202. In each embodiment, a second, distal rod, such as second rod 204, is operable to be received into a frangible U-shaped body, such as frangible U-shaped body 208, that is connected distally to the rod-to-rod connectors. In each embodiment, the orientations of the first and second rods may be set independently of each other.

Figure 18:
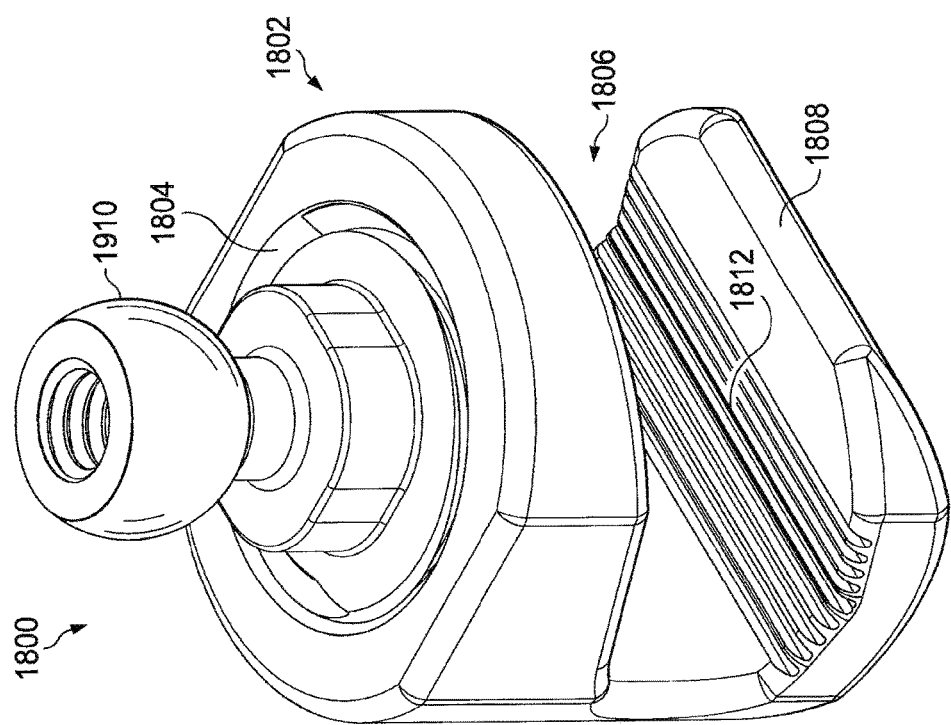
FIG. 18 depicts an elevation view of a J-hook rod connector, in accordance with one embodiment of the present disclosure.

FIG. 18 depicts an elevation view of a J-hook rod connector 1800, in accordance with one embodiment of the present disclosure. The J-hook rod connector 1800 comprises a body 1802 that may comprise a distal end and a proximal end. The distal end of the body 1802 may comprise a threaded aperture 1804 operable to receive a connector 1810 operable to connect the J-hook rod connector 1800 to a U-shaped body. The proximal end of the body 1802 may comprise a J-hook 1808 that creates a latitudinal opening 1806 operable to receive the first, proximal rod. The threaded aperture 1804 may extend into the opening 1806 such that the connector 1810 may come into contact with the first, proximal rod. A distal surface 1812 of the J-hook 1808 may be textured so as to prevent the first, proximal rod from slipping within the opening 1806.

In an embodiment, the connector 181 may comprise a distal orbital head and a proximal threaded portion. The distal orbital head may be operable to be received into a recess such as the recess 714 discussed in relation to the frangible U-shaped body 208 depicted in FIG. 7. The distal orbital head may comprise a recess or may be continuous. The proximal threaded portion may be operable to be threaded into the threaded aperture 1804 of the body 1802.

In operation, a first, proximal rod may be received within the opening 1806 in the body 1802. The connector 1810 may be threaded within and through the aperture 1804, until it locks the first, proximal rod into place relative to the body 1802. Next, a frangible U-shaped body may be received over the orbital head of the connector 1810 and a second, distal rod may be received within the frangible U-shaped body. Before a compression element is driven down and into the frangible U-shaped body and onto the second, distal rod, the frangible U-shaped body and the second, distal rod may be able to rotate independent of the orientation of the first, proximal rod. Once the desired orientation of the second, distal rod is achieved relative to the orientation of the first, proximal rod, the compression element may be driven against the second, distal rod, thereby locking the orientation of the second, distal rod relative to the first, proximal rod. The frangible sides of the frangible U-shaped body may then be removed, creating a lower-profile rod-to-rod cross connector.

Figure 19:
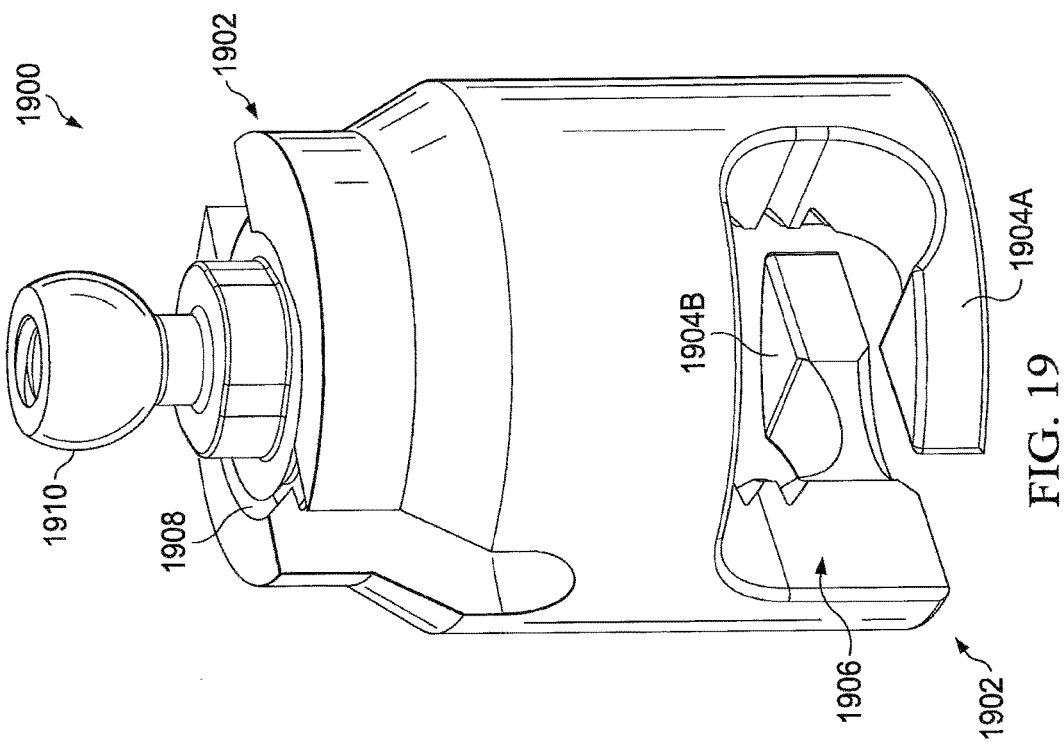
FIG. 19 depicts an elevation view of an integrated percutaneous head bayonet lock rod connector, in accordance with one embodiment of the present disclosure.

FIG. 19 depicts an elevation view of an integrated percutaneous head bayonet lock rod connector 1900, in accordance with one embodiment of the present disclosure. The integrated percutaneous head bayonet lock rod connector 1900 may comprise a body 1902 comprising a distal end and a proximal end. The proximal end of the body 1902 may comprise a first J-hook 1904A and a second J-hook 1904B that create a latitudinal opening 1906 operable to receive a first, proximal rod. The first and second J-hooks 1904A, 1904B may be designed with some play so that they may deform proximally to receive a rod and then snap back into place around the rod. The first and second J-hooks 1904A, 1904B may be spaced approximately 180° from each other about an outer circumference of the proximal end, with the first and second J-hooks 1904A, 19048 pointing in opposite directions.

The distal end of the body 1902 may comprise a threaded aperture 1908 operable to receive a connector 1910 operable to connect the bayonet lock rod connector 1900 to a U-shaped body. The threaded aperture 1908 may extend into the opening 1906 such that the connector 1910 may come into contact with the first, proximal rod.

In an embodiment, the connector 1910 may comprise a distal orbital head and a proximal threaded portion. The distal orbital head may be operable to be received into a recess such as the recess 714 discussed in relation to the frangible U-shaped body 208 depicted in FIG. 7. The distal orbital head may comprise a recess or may be continuous. The proximal threaded portion may be operable to be threaded into the threaded aperture 1904 of the body 1902.

In operation, a first, proximal rod may be received within the opening 1906 in the body 1902 and the body 1902 may be "turned" onto the rod. Next, the connector 1910 may be threaded within and through the aperture 1904, until it locks the first, proximal rod into place relative to the body 1902. Next, a frangible U-shaped body may be received over the orbital head of the connector 1910 and a second, distal rod may be received within the frangible U-shaped body. Before a compression element is driven down and into the frangible U-shaped body and onto the second, distal rod, the frangible U-shaped body and the second, distal rod may be able to rotate independent of the orientation of the first, proximal rod. Once the desired orientation of the second, distal rod is achieved relative to the orientation of the first, proximal rod, the compression element may be driven against the second, distal rod, thereby locking the orientation of the second, distal rod relative to the first, proximal rod. The frangible sides of the frangible U-shaped body may then be removed, creating a lower-profile rod-to-rod cross connector.

Figure 20:
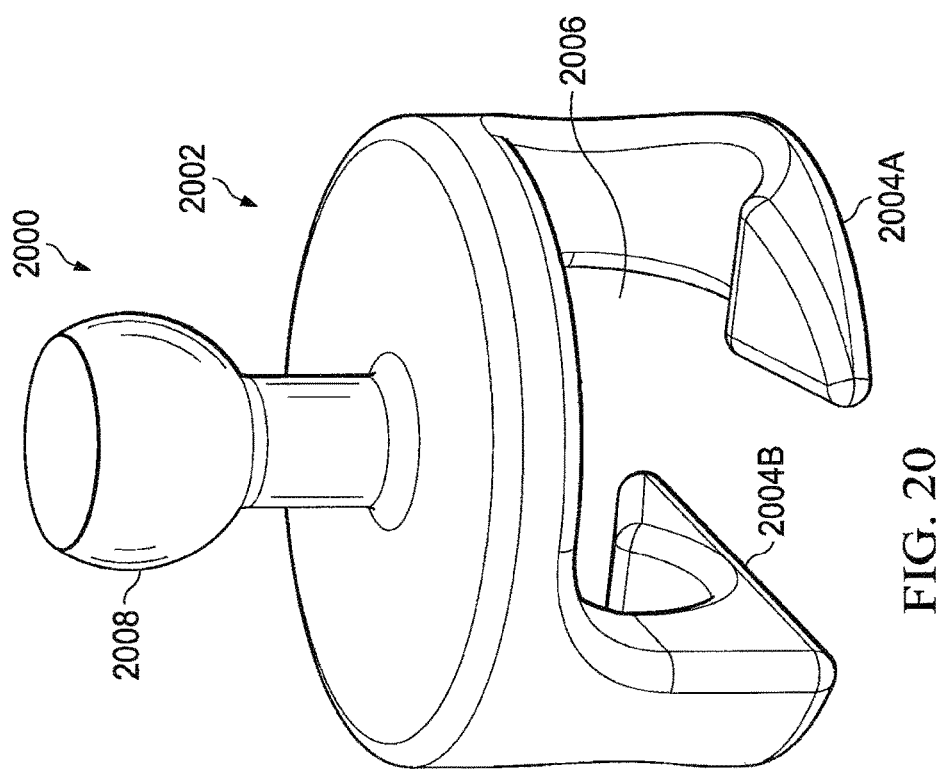
FIG. 20 depicts an elevation view of a snap style bayonet lock rod connector, in accordance with one embodiment of the present disclosure.

FIG. 20 depicts an elevation view of a snap style bayonet lock rod connector 2000, in accordance with one embodiment of the present disclosure. The snap style bayonet lock rod connector 2000 comprises a body 2002 that may comprise a distal end and a proximal end. The proximal end of the body 2002 may comprise a first J-hook 2004A and a second J-hook 2004B that create a latitudinal opening 2006 operable to receive a first, proximal rod. The first and second J-hooks 2004A, 2004B may be designed with some play so that they may deform proximally to receive a rod and then snap back into place around the rod. The first and second J-hooks 2004A, 2004B may be spaced approximately 180° from each other about an outer circumference of the proximal end, with the first and second J-hooks 2004A, 2004B pointing in opposite directions. The distal end of the body 2002 may comprise an integrated orbital head 2008, although in other embodiments a threaded connector may be inserted into the body.

In operation, a first, proximal rod may be received within the opening 2006 in the body 2002. The first, proximal rod may be "snapped" into place by inserting the rod into the opening 2006 between the first and second J-hooks 2004A, 2004B, then rotating the rod approximately 90°. The first and second J-hooks 2004A, 2004B are operable to deform proximally and then snap back into place around the rod, locking the rod into place relative to the body 2002. Next, a frangible U-shaped body may be received over the orbital head 2008 and a second, distal rod may be received within the frangible U-shaped body. Before a compression element is driven down and into the frangible U-shaped body and onto the second, distal rod, the frangible U-shaped body and the second, distal rod may be able to rotate independent of the orientation of the first, proximal rod. Once the desired orientation of the second, distal rod is achieved relative to the orientation of the first, proximal rod, the compression element may be driven against the second, distal rod, thereby locking the orientation of the second, distal rod relative to the first, proximal rod. The frangible sides of the frangible U-shaped body may then be removed, creating a lower-profile rod-to-rod cross connector.

Figure 21:
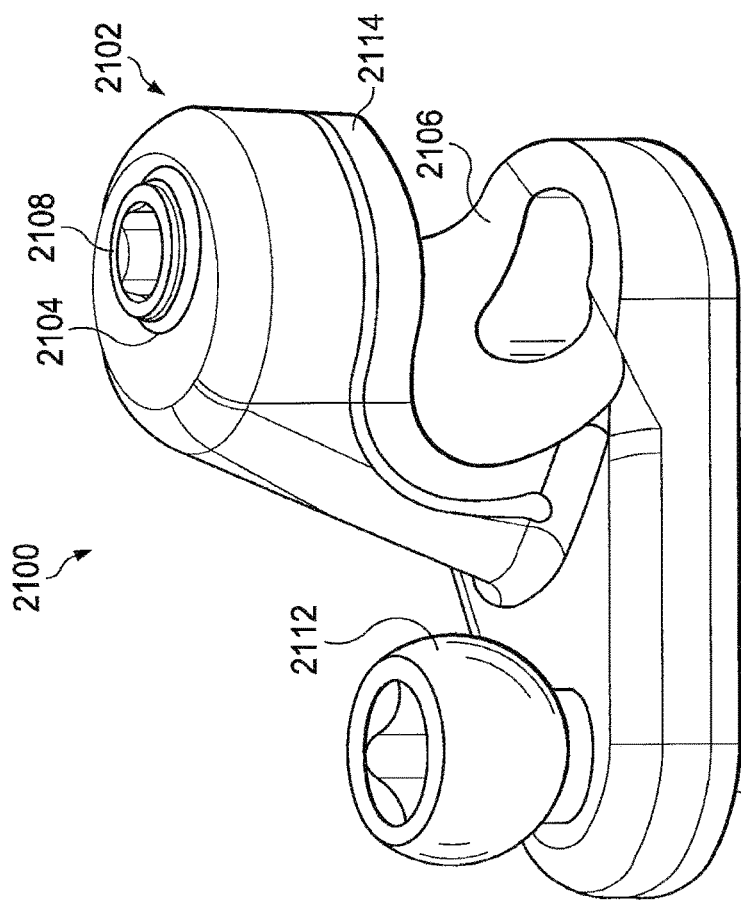
FIG. 21 depicts an elevation view of an offset ball rod connector, in accordance with one embodiment of the present disclosure.

FIG. 21 depicts an elevation view of an offset ball rod connector 2100, in accordance with one embodiment of the present disclosure. The offset ball rod connector 2100 comprises a body 2102 that may comprise a distal end and a proximal end. The distal end of the body 2102 may comprise a threaded aperture 2104 operable to receive a compression element 2108 that is operable to compress a spring feature 2114. The proximal end of the body 2102 may comprise a latitudinal opening 2106 operable to receive a first, proximal rod. The opening 2106 may be proximate to the spring feature 2114.

In an embodiment, the offset ball rod connector 2100 may further comprise an offset wing 2110 extending from the distal end of the body 2102. The offset wing 2110 may further comprise an orbital head 2112 extending distally from a distal surface of the offset wing 2110. As shown in FIG. 21, the orbital head 2112 on the offset wing 2110 is approximately the same height as the opening 2106. Therefore, when a frangible U-shaped body is received onto the orbital head 2112, the first and second rods create a low-profile construct.

In operation, a first, proximal rod may be received within the opening 2106 in the body 2102. The first, proximal rod may be locked into place relative to the body 2102 by driving the compression element 2108 proximally, thus engaging the spring feature 2114 against a distal surface of the first, proximal rod. Next, a frangible U-shaped body may be received over the orbital head 2112 and a second, distal rod may be received within the frangible U-shaped body. Before a compression element is driven down and into the frangible U-shaped body and onto the second, distal rod, the frangible U-shaped body and the second, distal rod may be able to rotate independent of the orientation of the first, proximal rod. Once the desired orientation of the second, distal rod is achieved relative to the orientation of the first, proximal rod, the compression element may be driven against the second, distal rod, thereby locking the orientation of the second, distal rod relative to the first, proximal rod. The frangible sides of the frangible U-shaped body may then be removed, creating a lower-profile rod-to-rod cross connector.

Figure 22:
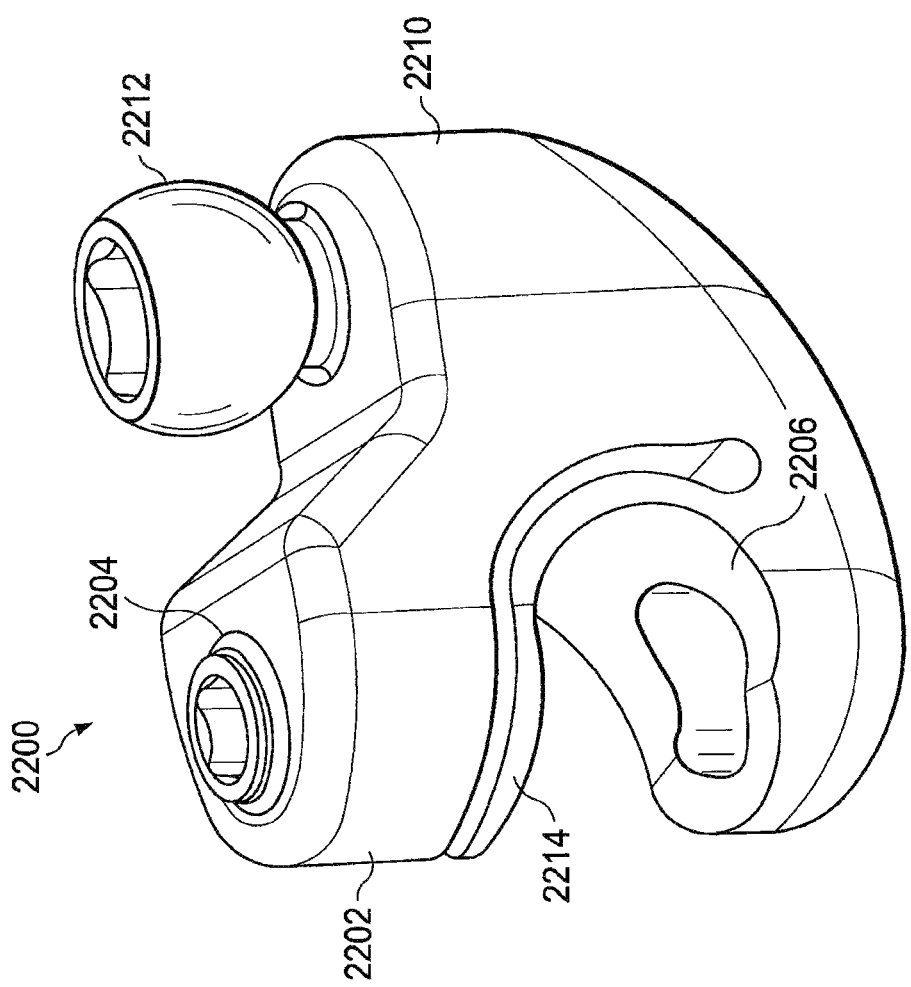
FIG. 22 depicts an elevation view of an offset ball rod connector, in accordance with one embodiment of the present disclosure.

FIG. 22 depicts an elevation view of an offset ball rod connector 2200, in accordance with one embodiment of the present disclosure. The offset ball rod connector 2200 comprises a body 2202 that may comprise a distal end and a proximal end. The distal end of the body 2202 may comprise a threaded aperture 2204 operable to receive a compression element 2208 that is operable to compress a spring feature 2214. The proximal end of the body 2202 may comprise a latitudinal opening 2206 operable to receive a first, proximal rod. The opening 2206 may be proximate to the spring feature 2214.

In an embodiment, the offset ball rod connector 2200 may further comprise an offset wing 2210 extending from the distal end of the body 2202. The offset wing 2210 may further comprise an orbital head 2212 extending distally from a distal surface of the offset wing 2210. As shown in FIG. 22, the orbital head 2212 on the offset wing 2210 is offset and above the opening 2206. Therefore, when a frangible U-shaped body is received onto the orbital head 2212, the first and second rods create a low-profile construct.

In operation, a first, proximal rod may be received within the opening 2206 in the body 2202. The first, proximal rod may be locked into place relative to the body 2202 by driving the compression element 2208 proximally, thus engaging the spring feature 2214 against a distal surface of the first, proximal rod. Next, a frangible U-shaped body may be received over the orbital head 2212 and a second, distal rod may be received within the frangible U-shaped body. Before a compression element is driven down and into the frangible U-shaped body and onto the second, distal rod, the frangible U-shaped body and the second, distal rod may be able to rotate independent of the orientation of the first, proximal rod. Once the desired orientation of the second, distal rod is achieved relative to the orientation of the first, proximal rod, the compression element may be driven against the second, distal rod, thereby locking the orientation of the second, distal rod relative to the first, proximal rod. The frangible sides of the frangible U-shaped body may then be removed, creating a lower-profile rod-to-rod cross connector.

Figure 23:
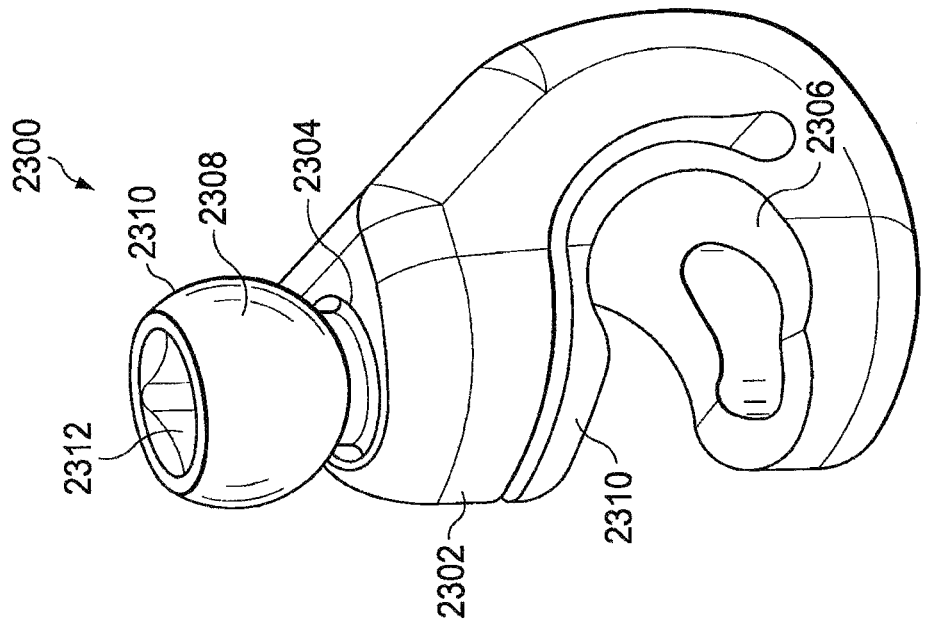
FIG. 23 depicts an elevation view of an offset ball rod connector, in accordance with one embodiment of the present disclosure.

FIG. 23 depicts an elevation view of an offset ball rod connector 2300, in accordance with one embodiment of the present disclosure. The offset ball rod connector 2300 comprises a body 2302 that may comprise a distal end and a proximal end. The distal end of the body 2302 may comprise a threaded aperture 2304 operable to receive a compression element 2308 that is operable to compress a spring feature 2114. In an embodiment, the compression element 2308 may further comprise an orbital head 2310 and a recess 2312. The proximal end of the body 2302 may comprise a latitudinal opening 2306 operable to receive a first, proximal rod. The opening 2306 may be proximate to the spring feature 2314.

In operation, a first, proximal rod may be received within the opening 2306 in the body 2302. The first, proximal rod may be locked into place relative to the body 2302 by driving the compression element 2308 proximally, thus engaging the spring feature 2314 against a distal surface of the first, proximal rod. Next, a frangible U-shaped body may be received over the orbital head 2310 and a second, distal rod may be received within the frangible U-shaped body. Before a compression element is driven down and into the frangible U-shaped body and onto the second, distal rod, the frangible U-shaped body and the second, distal rod may be able to rotate independent to the orientation of the first, proximal rod. Once the desired orientation of the second, distal rod is achieved relative to the orientation of the first, proximal rod, the compression element may be driven against the second, distal rod, thereby locking the orientation of the second, distal rod relative to the first, proximal rod. The frangible sides of the frangible U-shaped body may then be removed, creating a lower-profile rod-to-rod cross connector.

Figure 24:
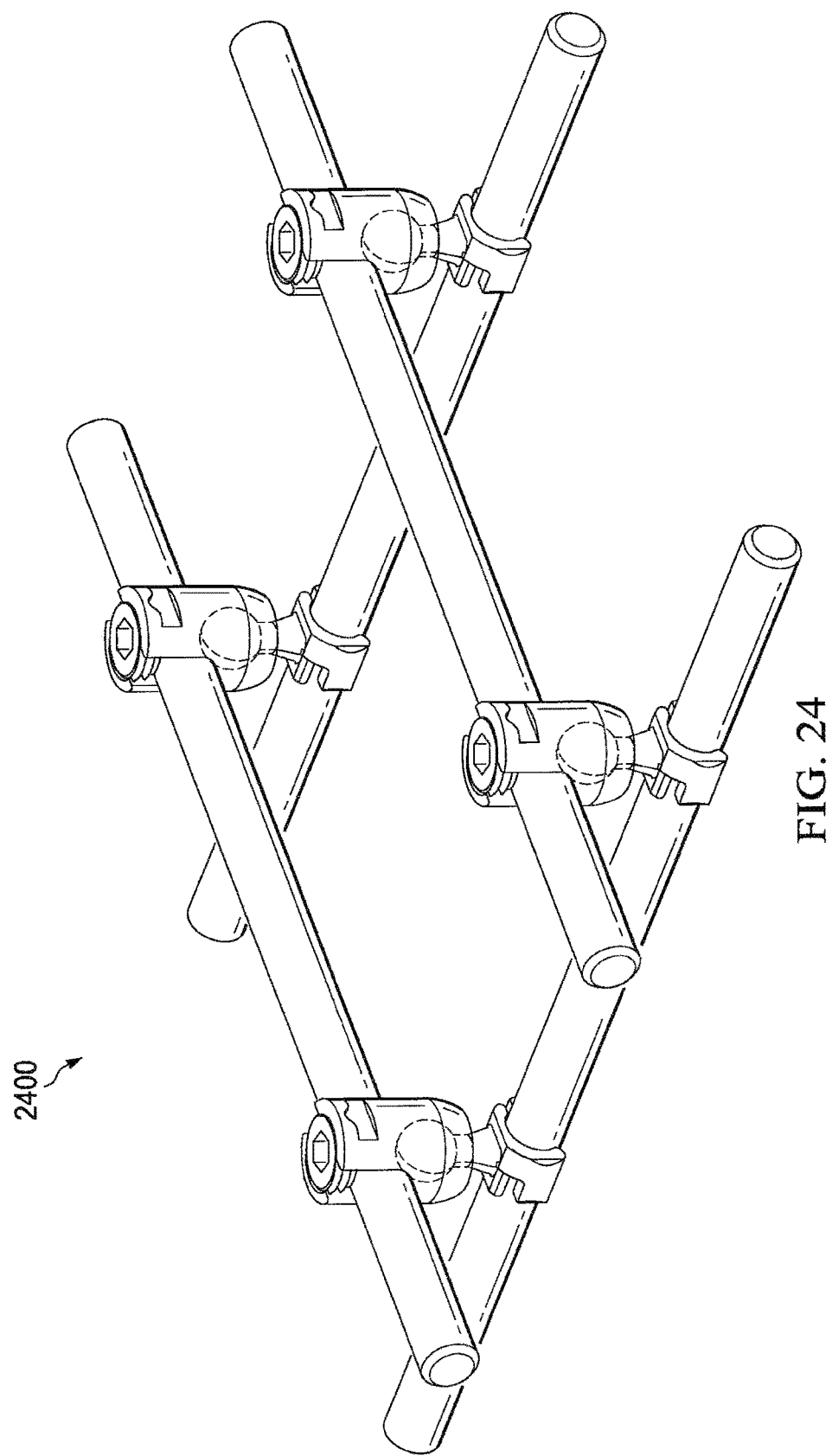
FIG. 24 depicts an elevation view of a rod-to-rod cross connecting system comprising four rods set in a square arrangement, in accordance with one embodiment of the present disclosure.

FIG. 24 depicts an elevation view of a rod-to-rod cross connecting system 2400 comprising four rods set in a rectangular arrangement, in accordance with one embodiment of the present disclosure. Using a combination of rods, U-shaped bodies, modular compression elements, and non-modular compression elements, the orientation of each rod may be set independent of the orientations of the remaining rods, and the rods may be set is a square or rectangular arrangement wherein adjacent rods are perpendicular to each other, or the rods may be set in a non-uniform arrangement wherein adjacent rods are not perpendicular to each other.

Figure 25:
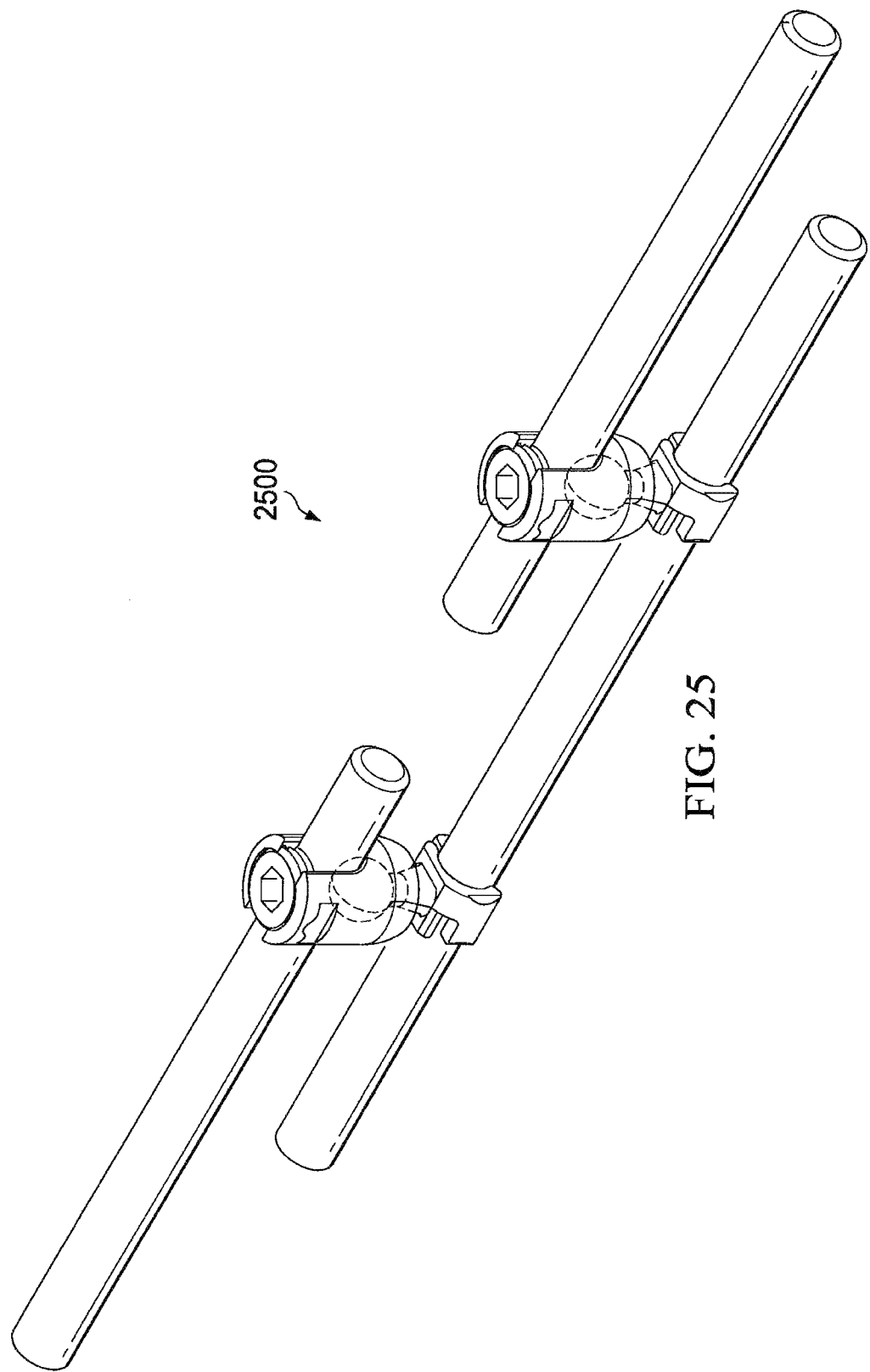
FIG. 25 depicts an elevation view of a ipsilateral construct extension system comprising two rods set in an in-line arrangement, in accordance with one embodiment of the present disclosure.

FIG. 25 depicts an elevation view of a ipsilateral construct extension system 2500 comprising three rods set in an in-line arrangement, in accordance with one embodiment of the present disclosure. In the ipsilateral construct extension arrangement, one or more extension rods may be used to extend a first rod, for example to adjacent spinal segments or the pelvis. Each extension rod may be affixed proximally or distally to a first construct comprising a combination of rods, U-shaped bodies, modular compression elements, and non-modular compression elements. While not shown in FIG. 25, each extension rod may be affixed to a second construct comprising a combination of rods, U-shaped bodies, modular compression elements, and non-modular compression elements, wherein the first construct and the second construct are located at opposite ends of the extension rod. The one or more extension rods may be implanted at the same time as the first rod or at a later time via either traditional, "open" surgical techniques or via minimally invasive surgical techniques.

It is to be understood that the previously described connectors may be used together in combination and like connectors do not have to be used together. For example, a pivoting modular split-orbital rod connector may be connected by a rod to a second pivoting modular split-orbital rod connector or may be connected by a rod to a sliding modular split-orbital rod connector or an offset jaw connector or any other known connector. In addition, any of the described connectors may be connected to a known U-shaped body connector either contralaterally or ipsilaterally.

Various sized rods, U-shaped bodies, fastener elements, modular compression elements, and non-modular compression elements may be employed in the embodiments depicted in FIGS. 2-22. One or more components of the modular rod-to-rod cross connecting systems disclosed herein may be made from any of the following materials: (a) any biocompatible material (which biocompatible material may be treated to permit bone ingrowth or prohibit bone ingrowth); (b) a plastic; (c) a fiber; (d) a polymer; (e) a metal (e.g., a pure metal such as titanium and/or an alloy such as Ti—Al—Nb, Tl-6Al-4V, stainless steel); or (f) any combination thereof.

While various embodiments in accordance with the principles disclosed herein have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

It will be understood that the principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

Additionally, the section headings herein are provided for consistency with the suggestions under 37 CPR 1.77 or otherwise to provide organizational cues. These headings shall not limit or characterize the invention(s) set out in any claims that may issue from this disclosure. Specifically and by way of example, although the headings refer to a "Feld of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. A percutaneous cross connector system for use with implantation rods, the system comprising:
   a rod attachment device comprising a first jaw portion and a second jaw portion;
   the first jaw portion comprising a first concave surface to engage with a surface of a rod, a first biasing member, and a first pivoting mechanism;

the second jaw portion comprising a second concave surface to engage with an opposite surface of the rod from the first jaw portion, a second pivoting mechanism, a second biasing surface, and a second locking surface;

wherein the first and second jaw portions can be mated so that the first and second concave surfaces are positioned on opposite sides of the rod, the first and second pivoting mechanisms are aligned to pivot on a common axis, and the first biasing member is engaged against the second biasing surface to drive the second jaw portion against the rod, a first U-shaped body having a proximal end and a distal end, wherein the proximal end is pivotally attached to the rod attachment device and the distal end comprises a threaded inner surface and is operable to receive a cross-connecting rod in a rod receiving channel;

a compression element having a threaded portion adapted to engage with the threaded inner surface of the U-shaped body and be driven adjacent to and against the cross-connecting rod, whereby when the compression element is driven against the cross connecting rod, the cross-connecting rod is driven against the second locking surface of the second jaw portion, thus locking the second jaw portion against the rod; and a retention ring, wherein the first jaw portion comprises a first annular recess, wherein the proximal end of the first U-shaped body comprises a second annular recess, and wherein the retention ring is mated within the first and second annular recesses when the first jaw portion is pivotally attached to the first U-shaped body.

2. The rod attachment device according to claim 1, wherein the retention ring comprises an arcuate member having a radius of at least 120 degrees.

3. The rod attachment device according to claim 1, further comprising a pressure cap having a proximal end and a distal end, wherein the proximal end has a proximal surface adapted to adjoin the second locking surface of the second jaw portion, wherein the distal end of the pressure cap comprises a u-shaped surface adapted to receive a cross-connecting rod, wherein the pressure cap is adapted to be slidably attached within the first U-shaped body such that the u-shaped surface is substantially aligned with the first U-shaped body; whereby when the compression element is driven against the cross connecting rod, the cross-connecting rod is driven against the second locking surface of the second jaw portion, thus locking the second jaw portion against the rod.

4. The rod attachment device according to claim 3, wherein the proximal surface of the pressure cap comprises a flat surface and the distal end of the pressure cap comprises a saddle shape having a radius substantially similar to the radius of the rod.

5. The rod attachment device according to claim 4, wherein the pressure cap further comprises at least one chordal surface passing from the proximal end to the distal end, and wherein the proximal end of the u-shaped body comprises at least one chordal surface adapted to mate with the at least one chordal surface of the pressure cap so that the pressure cap may slide within the u-shaped member without rotating.

6. The rod attachment device according to claim 1, wherein the first and second concave surfaces of the rod attachment device comprise an arc greater than about 180 degrees.

7. The rod attachment device according to claim 1, wherein the first concave surface of the first jaw portion comprises an arc of about 60 degrees.

8. The rod attachment device according to claim 1, wherein the second concave surface of the second jaw portion comprises an arc of about 150 degrees.

9. The percutaneous cross connector system according to claim 1, wherein the first U-shaped body comprises first and second body sides, first and second removable arms, and first and second frangible tabs.

10. The percutaneous cross connector system according to claim 9, wherein the first and second frangible tabs are operable to be broken off from the first and second removable arms, and the first and second removable arms are operable to be splayed away from the first and second body sides.

11. A method for implanting a percutaneous cross connector system, the method comprising:

providing a rod attachment device comprising a first jaw portion and a second jaw portion, the rod attachment device further comprising:

the first jaw portion comprising a first concave surface, a first biasing member, and a first pivoting mechanism;

the second jaw portion comprising a second concave surface, a second pivoting mechanism, a second biasing surface, and a second locking surface;

engaging a surface of a rod with the first concave surface of the first jaw portion and engaging an opposite surface of the rod with the second concave surface of the second jaw portion;

mating the first and second jaw portions so that the first and second concave surfaces are positioned on opposite sides of the rod, and the first and second pivoting mechanisms are aligned to pivot on a common axis;

engaging the first biasing member against the second biasing surface and driving the second jaw portion against the rod;

pivotally attaching a first U-shaped body to the rod attachment device, the first U-shaped body having a proximal end and a distal end, and the distal end having a threaded inner surface and is operable to receive a cross-connecting rod in a rod receiving channel; and driving a compression element against the cross-connecting rod, the compression element having a threaded portion adapted to engage with the threaded inner surface of the U-shaped body and be driven adjacent to and against the cross-connecting rod;

whereby when the compression element is driven against the cross connecting rod, the cross-connecting rod is driven against the second locking surface of the second jaw portion, thus locking the second jaw portion against the rod; and further comprising a retention ring, wherein the first jaw portion comprises a first annular recess, wherein the proximal end or first U-shaped body comprises a second annular recess, and wherein the retention ring is mated within the first and second annular recesses when the first jaw portion is pivotally attached to the first U-shaped body.

12. The method according to claim 11, wherein the retention ring comprises an arcuate member having a radius of at least 120 degrees.

13. The method according to claim 11, further comprising driving the cross-connecting rod against a pressure cap, the pressure cap having a proximal end and a distal end, wherein the proximal end has a proximal surface adapted to adjoin the second locking surface of the second jaw portion, wherein the distal end of the pressure cap comprises a u-shaped surface adapted to receive a cross-connecting rod, wherein the pressure cap is adapted to be slidably attached within the first U-shaped body such that the u-shaped surface is substantially aligned with the first U-shaped body, whereby when the compression element is driven against the cross connecting rod, the cross-connecting rod is driven against the pressure cap, thereby driving the proximal surface of the pressure cap against the second locking surface of the second jaw portion, thus locking the second jaw portion against the rod.

14. The method according to claim 13, wherein the proximal surface of the pressure cap comprises a flat surface and the distal end of the pressure cap comprises a saddle shape having a radius substantially similar to the radius of the rod.

15. The method according to claim 14, wherein the pressure cap further comprises at least one chordal surface passing from the proximal end to the distal end, and wherein the proximal end of the u-shaped body comprises at least one chordal surface adapted to mate with the at least one chordal surface of the pressure cap so that the pressure cap may slide within the u-shaped member without rotating.

16. The method according to claim 11, wherein the first and second concave surfaces of the rod attachment device comprise an arc greater than about 180 degrees.

17. The method according to claim 11, wherein the fast concave surface of the first jaw portion comprises an arc of about 60 degrees.

18. The method according to claim 11, wherein the second concave surface of the second jaw portion comprises an arc of about 150 degrees.

19. The method according to claim 11, wherein the first U-shaped body comprises first and second body sides, first and second removable arms, and first and second frangible tabs.

20. The method according to claim 19, wherein the first and second frangible tabs are operable to be broken off from the first and second removable arms, and the first and second removable arms are operable to be splayed away from the first and second body sides.

21. A percutaneous cross connector system for use with implantation rods, the system comprising:
a rod attachment device having a split-orbital head at one end and a rod attachment claw at an opposite end, the rod attachment device comprising:
a first claw portion comprising a first concave surface to engage with a surface of a rod, a first orbital head portion comprising a portion of the split-orbital head, and a first pivoting mechanism disposed between the first claw portion and the first orbital head portion;
a second claw portion comprising a second concave surface to engage with an opposite surface of the rod from the first claw portion, a second orbital head portion comprising a portion of the split-orbital head, and a second pivoting mechanism disposed between the second claw portion and the second orbital head portion;
wherein the first and second claw portion s can be mated so that the first and second orbital head portions substantially align to form the split-orbital head, the first and second concave surfaces are aligned opposite each other, and the first and second pivoting mechanisms are aligned to pivot on a common axis,
whereby when the first and second orbital head portions are placed in substantial circumferential alignment, the first and second concave surfaces are displaced towards each other;
a first u-shaped body having a proximal end and a distal end, wherein the proximal end is operable to receive the split-orbital head of the rod attachment device, and the distal end comprises a threaded inner surface and is operable to receive a cross-connecting rod in a rod receiving channel;
a retaining ring having a conical shape adapted to be mounted within the proximal end of the u-shaped body, wherein an interior surface of the retaining ring is adapted to be mated with a proximal end of the split orbital head; and
a compression element having a threaded portion adapted to engage with the threaded inner surface of the u-shaped body so that the compression element can be driven adjacent to and against the cross-connecting rod, whereby when the compression element is driven against the cross connecting rod, the cross-connecting rod is driven against the split orbital head and the conical retaining ring, thus bringing the split orbital head into substantial circumferential alignment.

22. A percutaneous cross connector system for use with implantation rods, the system comprising:
a rod attachment device having a split-orbital head at one end and a rod attachment claw at an opposite end, the rod attachment device comprising:
a first claw portion comprising a first concave surface to engage with a surface of a rod, a first orbital head portion comprising a portion of the split-orbital head, and a first sliding mechanism disposed between the first claw portion and the first orbital head portion;
a second claw portion comprising a second concave surface to engage with an opposite surface of the rod from the first claw portion, a second orbital head portion comprising a portion of the split-orbital head, and a second sliding mechanism disposed between the second claw portion and the second orbital head portion;
wherein the first and second sliding mechanism can be mated so that the first and second orbital head portions substantially align to form the split-orbital head, and the first and second concave surfaces are aligned opposite each other,
whereby when the first and second orbital head portions are placed in substantial circumferential alignment, the first and second concave surfaces are displaced towards each other;
a first u-shaped body having a distal end and a proximal end, wherein the proximal end is operable to receive the split-orbital head of the rod attachment device, and wherein the distal end comprises a threaded inner surface and is operable to receive a cross-connecting rod in a rod receiving channel in a distal end;
a retaining ring having a conical shape adapted to be mounted within the proximal end of the u-shaped body, wherein an interior surface of the retaining ring is adapted to be mated with a proximal end of the split orbital head; and
a compression element having a threaded portion adapted to engage with the threaded inner surface of the u-shaped body so that the compression element can be driven adjacent to and against the cross-connecting rod, whereby when the compression element is driven against the cross connecting rod, the cross-connecting rod is driven against the split orbital head and the conical retaining ring, thus bringing the split orbital head into substantial circumferential alignment.

\* \* \* \* \*